(12) United States Patent
Joshi

(10) Patent No.: US 10,687,536 B2
(45) Date of Patent: Jun. 23, 2020

(54) DISPOSABLE WIPES FOR ENERGIZED TREATMENT AGENT

(71) Applicant: Microlin, LLC, Salt Lake City, UT (US)

(72) Inventor: Ashok V. Joshi, Salt Lake City, UT (US)

(73) Assignee: Microlin, LLC, Salt Lake City, UT (US)

( * ) Notice: Subject to any disclaimer, the term of this patent is extended or adjusted under 35 U.S.C. 154(b) by 349 days.

(21) Appl. No.: 15/435,116

(22) Filed: Feb. 16, 2017

(65) Prior Publication Data

US 2017/0156336 A1    Jun. 8, 2017

Related U.S. Application Data

(63) Continuation-in-part of application No. PCT/US2015/067540, filed on Dec. 27, 2015, which
(Continued)

(51) Int. Cl.
*C25B 1/02* (2006.01)
*C25B 3/04* (2006.01)
(Continued)

(52) U.S. Cl.
CPC .............. *A01N 59/00* (2013.01); *A01N 25/34* (2013.01); *A01N 33/12* (2013.01); *A01N 43/66* (2013.01);
(Continued)

(58) Field of Classification Search
CPC .. C25B 9/06; C25B 1/26; A01N 43/66; A01N 59/02; A01N 59/00; A01N 33/12; A01N 59/16
(Continued)

(56) References Cited

U.S. PATENT DOCUMENTS

| 5,126,070 A | 6/1992 | Leifheit et al. |
| 5,335,478 A | 8/1994 | Aronsen |

(Continued)

FOREIGN PATENT DOCUMENTS

| EP | 2168604 | 3/2010 |
| EP | 2168604 A1 | 3/2010 |

(Continued)

OTHER PUBLICATIONS

Plasma Based Sterilization: Overview and the Stepwise Inactivation Process of Microbial by Non-thermal Atmospheric Pressure Plasma Jet; International Journal of Engineering & Technology IJET-IJENS vol. 14 No. 05.

(Continued)

*Primary Examiner* — Zulmariam Mendez
(74) *Attorney, Agent, or Firm* — Brian C. Trask

(57) ABSTRACT

A disposable, single-use wipe that can be used deodorize, disinfect, and/or sterilize an object. A wipe includes a flexible membrane or cloth-like element that may apply, distribute, and/or remove a treatment agent to, over, or from a surface of the object. A treatment agent, such as micron-, or nano-sized particles of a disinfectant or sterilant chemical, Ozone, negative ions, Hydroxyl radicals, or alcohol, etc., may be applied to the surface by the wipe or another applicator. An additional treatment agent (e.g., Triclosan, Chlorine dioxide, Hydroxyl radicals, etc.), may be associated with a wipe to enhance biocidal activity. The wipe may be used alone, in combination with a holder, or in combination with an applicator of energized treatment agent. An applicator and/or a holder may be used to energize one or more treatment agent to improve its efficacy.

13 Claims, 14 Drawing Sheets

Related U.S. Application Data is a continuation-in-part of application No. 14/314,862, filed on Jun. 25, 2014, now Pat. No. 9,603,359.

(60) Provisional application No. 62/164,640, filed on May 21, 2015, provisional application No. 62/098,277, filed on Dec. 30, 2014, provisional application No. 61/846,164, filed on Jul. 15, 2013, provisional application No. 61/839,986, filed on Jun. 27, 2013.

(51) Int. Cl.
| | |
|---|---|
| *C25B 9/04* | (2006.01) |
| *C25B 7/00* | (2006.01) |
| *A01N 59/00* | (2006.01) |
| *A61L 2/235* | (2006.01) |
| *A01N 25/34* | (2006.01) |
| *A01N 59/02* | (2006.01) |
| *A01N 59/16* | (2006.01) |
| *C25B 9/06* | (2006.01) |
| *C25B 1/26* | (2006.01) |
| *A01N 43/66* | (2006.01) |
| *A61L 2/03* | (2006.01) |
| *A01N 33/12* | (2006.01) |

(52) U.S. Cl.
CPC ............. *A01N 59/02* (2013.01); *A01N 59/16* (2013.01); *A61L 2/035* (2013.01); *A61L 2/235* (2013.01); *C25B 1/26* (2013.01); *C25B 9/06* (2013.01); *A61L 2202/11* (2013.01); *A61L 2202/15* (2013.01)

(58) Field of Classification Search
USPC ........................................................ 204/242
See application file for complete search history.

(56) References Cited

U.S. PATENT DOCUMENTS

| | | | |
|---|---|---|---|
| 5,407,685 | A | 4/1995 | Malchesky et al. |
| 6,916,480 | B2 | 7/2005 | Anderson et al. |
| 9,433,474 | B2 | 9/2016 | Swinney |
| 2005/0079987 | A1 | 4/2005 | Cartwright et al. |
| 2005/0187580 | A1 | 8/2005 | Skiba |
| 2005/0202066 | A1 | 9/2005 | Arata |
| 2006/0039840 | A1 | 2/2006 | Chia et al. |
| 2010/0078318 | A1 | 4/2010 | Huffman |
| 2011/0085934 | A1* | 4/2011 | Joshi ................. A23L 3/3409 422/5 |
| 2011/0118655 | A1 | 5/2011 | Fassih et al. |

FOREIGN PATENT DOCUMENTS

| | | |
|---|---|---|
| EP | 2498867 | 9/2012 |
| JP | 2006-189883 A | 7/1994 |
| WO | 94/26317 | 11/1994 |
| WO | 03-070004 A1 | 8/2003 |
| WO | 2005/107823 | 11/2005 |
| WO | 2011/044355 | 4/2011 |
| WO | 2011059915 | 5/2011 |
| WO | 2014/210164 | 12/2014 |
| WO | 2014210164 | 12/2014 |

OTHER PUBLICATIONS

Surface Micro-Discharge (SMD)—Analysis of the Antimicrobial Effect and the Plasma Chemistry; Dissertation; der Fakultät für Physik der Ludwig-Maximillians-Universität München zur Erlangung des Grades eines Doktors der Naturwissenschaften; Jin Jeon.

Cold Atmospheric Air Plasma Sterilization against Spores and Other Microorganisms of Clinical Interest; Appl Environ Microbiol. Aug. 2012; 78(15): 5077-5082. doi: 10.1128/AEM.00583-12; Tobias G. Klämpfl, Georg Isbary, Tetsuji Shimizu, Yang-Fang Li, Julia L. Zimmermann, Wilhelm Stolz, Jürgen Schlegel, Gregor E. Morfill, and Hans-Ulrich Schmidt.

International Search Report and the Written Opinion of the International Searching Authority; dated Jul. 15, 2016.

Nho "Written Opinion of the International Searching Authority" Application No. PCT/US2014/044111, 9 pages, dated Oct. 21, 2014.

International Search report and Written Opinion for PCT/US2015/67540, dated Jul. 15, 2016.

Extended European Search Report, dated Feb. 17, 2017.

Extended European Search Report, dated Sep. 15, 2017.

* cited by examiner

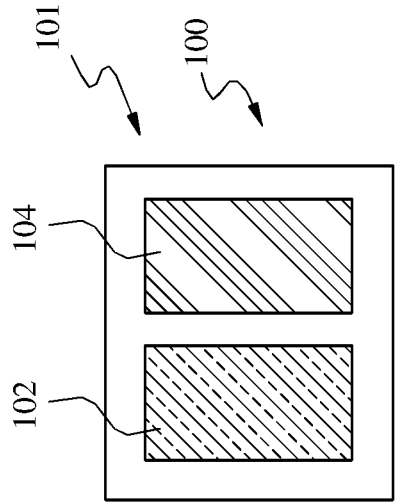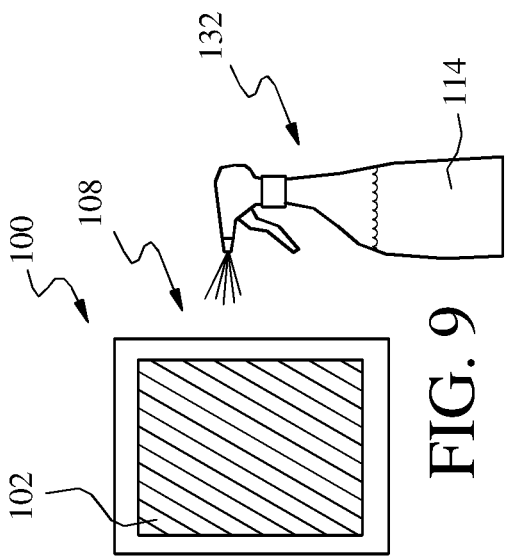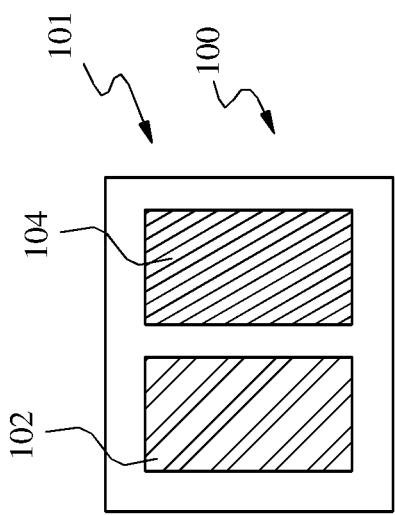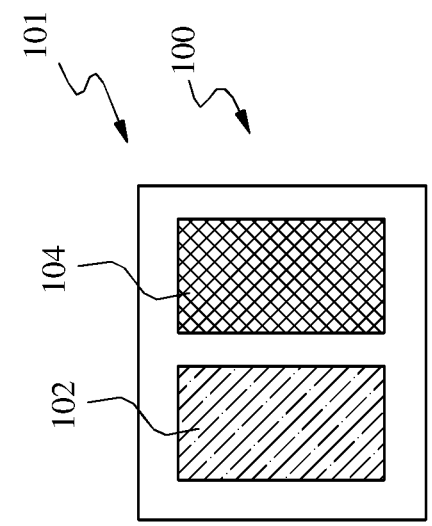

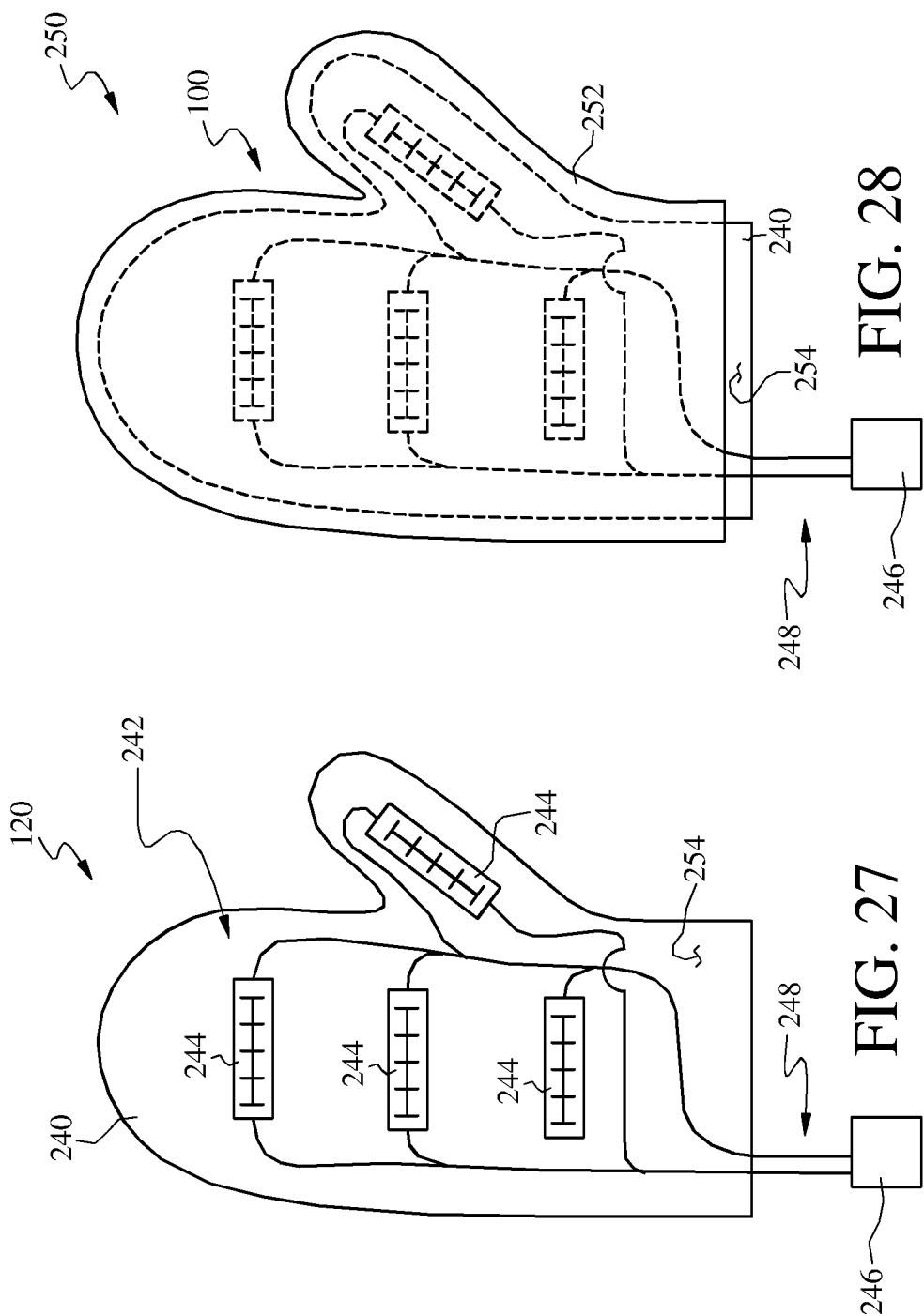

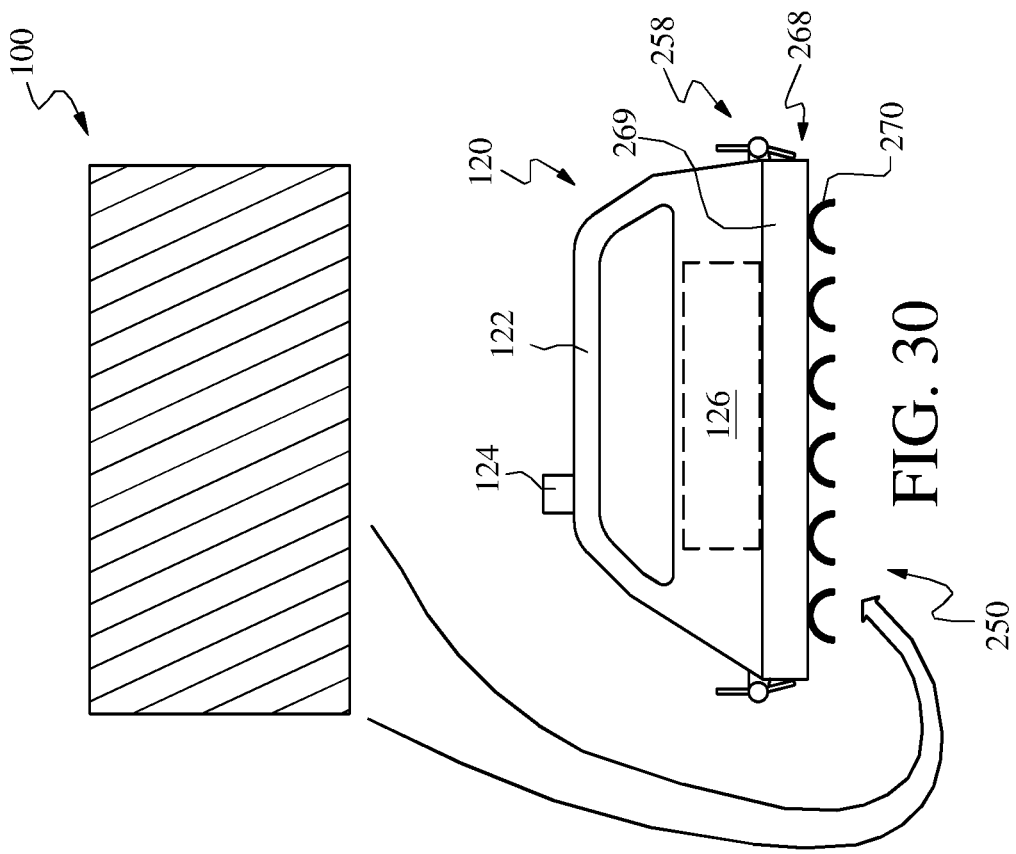
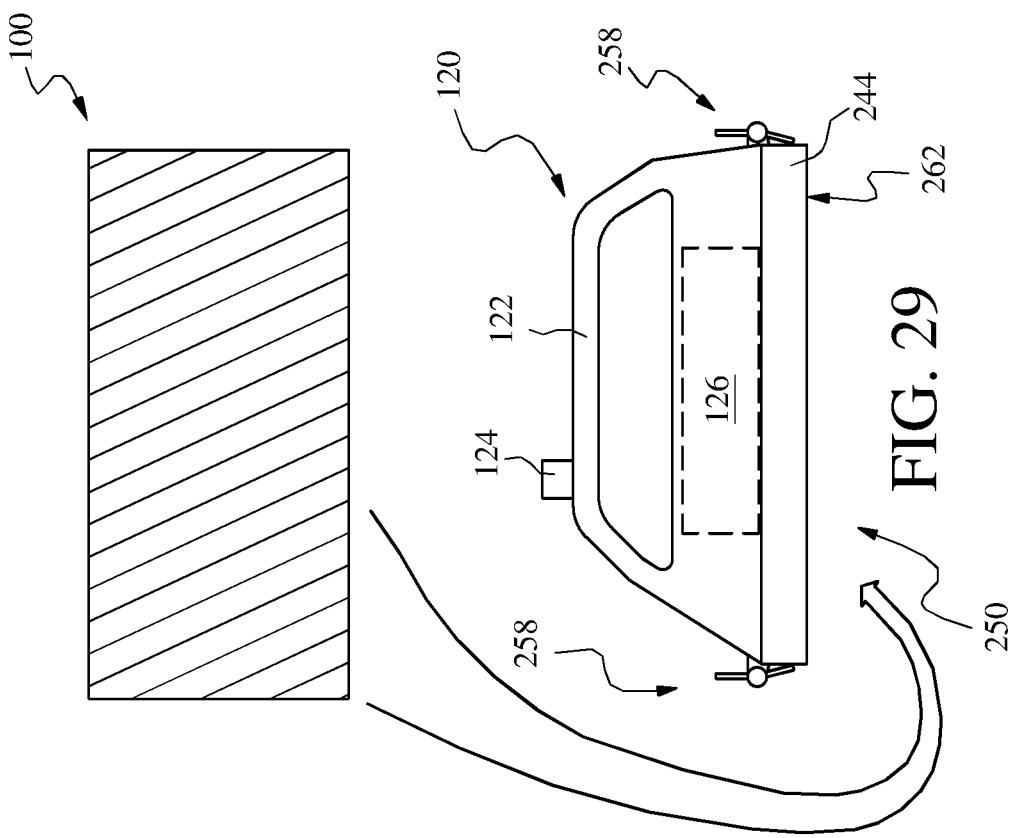

DISPOSABLE WIPES FOR ENERGIZED TREATMENT AGENT

PRIORITY CLAIM

This application is a continuation-in-part of the International Application Serial No. PCT/US2015/067540, filed Dec. 27, 2015, titled "DISPOSABLE WIPES FOR OPTIONAL DISINFECTION, DEODORIZATION, AND/OR STERILIZATION AND METHODS OF USE THEREOF", which claims the benefit of the filing dates of U.S. Provisional Patent Application Ser. No. 62/098,277, filed Dec. 30, 2014, entitled "DISPOSABLE WIPES FOR OPTIONAL DISINFECTION, DEODORIZATION, AND/OR STERILIZATION", and Ser. No. 62/164,640, filed on May 21, 2015, and also entitled "DISPOSABLE WIPES FOR OPTIONAL DISINFECTION, DEODORIZATION, AND/OR STERILIZATION"; this application is also a continuation-in-part of U.S. utility application Ser. No. 14/314,862, titled "ANTI-MICROBIAL DISINFECTANT WIPE AND METHOD OF USE", filed on Jun. 25, 2014, which claims the benefit of the filing dates of U.S. Provisional Patent Application Ser. No. 61/839,986, filed on Jun. 27, 2013, titled "ANTI-MICROBIAL DISINFECTANT WIPE AND METHOD OF USE", and Ser. No. 61/846,164, filed on Jul. 15, 2013, titled "ELECTROCHEMICALLY-ACTIVATED ANTI-MICROBIAL DISINFECTANT WIPE AND METHOD OF USE", each of which is incorporated by this reference as though set forth herein in their entirety.

TECHNICAL FIELD

This invention relates to apparatus and methods for optionally disinfecting, deodorizing, and/or sterilizing various objects by wiping the object with a treatment wipe. Embodiments may include a wipe holder that is structured to improve the efficacy of e.g., commercially available disinfecting wipes. Certain wipe holders energize treatment agent to promote the presence of hydroxyl radicals, or ions, such as Silver ions or chloride ions, or introduce micro-, micron- or nano-sized particles of treatment agent, at the time and place of desired treatment. Sometimes, an applicator is used to apply energized treatment agent to a surface, and a wipe may spread and/or remove treatment agent from the surface.

BACKGROUND

Currently, a wide range of equipment and methods are available to disinfect or sterilize objects and surfaces in residential, industrial, commercial, hospital, hotel, and food processing environments. Exemplary treatment devices for treatment of objects, and methods of use for those treatment devices, are disclosed in U.S. Pat. No. 7,892,486, the entire contents of which are hereby incorporated as a portion of this disclosure by reference. A document disclosing characterization and use of Peroxone as a treatment substance is available on the world wide web at epa.gov/ogwdw/mdbp/pdf/alter/chapt_7.pdf. Although directed generally toward treatment of water, the aforementioned document is also incorporated by reference as a portion of this disclosure. Various chemical reactions and structures for generating Hydroxyl radicals and other deodorizing, disinfecting, and/or sterilizing elements are disclosed in U.S. Provisional Patent Application No. 62/090,799, the entire disclosure of which is also hereby incorporated by reference as a portion of this disclosure.

Unfortunately, the state of the art products and equipment for disinfecting, deodorizing and/or sterilizing are confined to products best suited to use in a commercial or industrial environment, due to increased expense and cumbersome methods and chemicals. In view of the foregoing, what is needed are products, equipment and methods for treating (e.g. disinfecting, deodorizing, and/or sterilizing) surfaces of objects which are simple to use, less expensive, and more environmentally friendly.

DISCLOSURE OF THE INVENTION

The invention may be embodied to provide a one-time-use, disposable wipe for use in optionally deodorizing, disinfecting, or sterilizing an object. An exemplary wipe includes a first substrate comprising a flexible membrane. Typically, a first treatment agent, such as a chemical element or compound, is either associable with, or carried by, the first substrate. A second chemical element or compound may also either be associable with, or carried by, the first substrate. In one embodiment, the first substrate is structured to carry a treatment agent formed as a product of a chemical reaction resulting from combination of a first chemical element or compound and a second chemical element or compound at the time of use, and at the location of use, of the wipe to deodorize, disinfect, and/or sterilize an object. In certain preferred embodiments, a treatment agent includes a Hydroxyl radical.

In one embodiment of a wipe, the first chemical element or compound is carried by a first substrate, and the second chemical element or compound is also carried by the first substrate. Desirably, the first and second chemical element or compound are selected from chemically reactive couples structured such that fluid applied to the first substrate is effective to cause the chemical reaction, and consequently, to produce the treatment agent. A workable fluid may include water. The first chemical element or compound and the second chemical element or compound can be selected a make a couple set forth in the group consisting of (Sodium Chlorate and Citric acid; Citric acid and Silver Citrate; Alkali-Percarbonate and Magnesium Oxide; Sodium Chlorite and Citric acid; Quaternary Ammonium Salt and Calcium Hypochlorite; Alkali-perchlorate and UV light; Silver Chloride and UV light; Iron Sulfate and Alkali-percarbonate; stable Hydrogen Peroxide and Iron Sulfate; Hydrogen Peroxide and Silver Nitrate; and Hydrogen Peroxide and Alcohol specifically including Benzyl alcohol).

In another embodiment, the first chemical element or compound is carried by the first substrate, and the second chemical element or compound is carried by a dispenser independent from the first substrate. That dispenser is generally structured to apply the second chemical element or compound to the substrate. Again, the first and second chemical element or compound may be selected from chemically reactive couples such that application of the second chemical element or compound by the dispenser to the first substrate is effective to cause a chemical reaction that forms a treatment agent.

In another embodiment, both of the first and second chemical element or compound are carried by a dispenser independent from the first substrate. The dispenser can be structured to apply the first and second chemical element or compound to the first substrate. Again, the first and second chemical element or compound are typically selected from chemically reactive couples such that application of the first and second chemical element or compound by the dispenser to the first substrate is effective to cause the chemical reaction. One exemplary dispenser includes a spray bottle, which can be a multi-compartment bottle.

Sometimes, a biocidal compound or element may carried on a wipe, or otherwise introduced to a treatment area by an applicator. A workable biocidal compound or element may be selected from the group including (Triclosan; Chlorine dioxide; Hydroxyl radicals; Silver citrate; Sodium Chlorate or Sodium Chlorite; Alkali percarbonate; or Sodium dichloroisocynurate; and quaternary ammonium compounds).

In another embodiment, a wipe may be formed by stacking in physical contact, or juxtaposing, a plurality of substrates. For example, a first chemical element or compound may be carried by a first substrate, and a second chemical element or compound may be carried by a second substrate. Desirably, the first and second chemical element or compound are selected from chemically reactive couples structured such that juxtaposition of the first and second substrates in the presence of moisture can be effective to cause a chemical reaction that produces a desired treatment agent. Sometimes, the chemical reaction may further require application of moisture to the wipe.

A multi-layer wipe may be formed by extraction of a plurality of prepared substrates from one or more dispenser. In one example, a dispenser may include a first chamber and a second chamber. The first chamber may hold a plurality of substrates, each such substrate being removable from the first chamber to form a first substrate. The second chamber can also hold a plurality of substrates, each such substrate being removable to form a second substrate. In a preferred arrangement, a dispenser is structured to facilitate simultaneous dispensation of substrates from a first compartment and a second compartment to produce successive sets of juxtaposed first and second substrates.

A wipe may sometimes be used with a holder structured to cause a chemical reaction that makes a treatment agent. Sometimes, a holder may operate on a treatment agent to place the agent into a more reactive, or effective form. For example, a holder may cause a treatment agent to be dispersed into micro-, micron-, or nano-sized particles that may then be applied to the surface to be treated. A wipe may also, or alternatively, be used with a holder structured to impart an electrical charge onto the wipe, and/or introduce a plasma to the wipe and its treatment agent effective to produce a chemical compound in radical form. A holder may even be configured to permit the plasma, or an alternative output from an energizing transducer, to participate in treatment of an object for deodorizing, disinfecting, and/or sterilizing. In certain cases, a biocidal agent may be advantageously included in the wipe. Sometimes, a wipe includes or carries a biocidal agent, and also may be structured to cause an on-board electrical charge generation operable to attract gram positive and/or negative microbes to the biocidal agent.

In an alternative embodiment, an applicator may be employed to cause a fluidized treatment agent to be dispersed into micro-, micron-, or nano-sized particles that may then be applied to the surface to be treated, and a wipe may be used to spread the treatment agent and/or remove the agent from the surface. In that case, a wipe may be embodied in a simple paper towel, cotton cloth, or in some other fluid-absorbent membrane-like element.

Certain wipes can be used by activating a wipe to cause a chemical or physical reaction, and treating an object by physically spreading an energized treatment agent, formed as a product of a chemical reaction or as a consequence of a physical change imparted to the treatment agent, onto the object with the wipe. On the other hand, certain wipes may be substantially inert. An exemplary inert wipe may be used to spread energized treatment agent over, and/or remove energized treatment agent from, a surface. Preferred treatment agents include Hydroxyl radicals and micron- or nano-sized particles of disinfectant chemicals. Operable disinfectant chemicals may include an Alcohol, Hydrogen Peroxide, Ammonium Quaternary compounds, or bleaches such as Sodium Hypochlorite. A biocidal agent may be included in a wipe to further enhance destruction of bacteria and microbes.

BRIEF DESCRIPTION OF THE DRAWINGS

In the drawings, which illustrate what are currently regarded as the best modes for carrying out the invention:

FIG. 6 is a pictorial view in elevation of a sixth disposable wipe;

FIG. 7 is a pictorial view in elevation of a seventh disposable wipe;

FIG. 8 is a pictorial view in elevation of a eighth disposable wipe;

FIGS. 9 through 13 are pictorial views in elevation of additional disposable wipes, each wipe being in combination with a spray bottle of solution;

FIG. 27 is a pictorial view of a workable energizing wipe holder that is compliant to accommodate to irregular or non-flat surfaces;

FIG. 28 illustrates a wipe installed on the embodiment of FIG. 27;

FIG. 29 is a pictorial view of another embodiment, generally illustrating one or more energizing transducers associated with a holder, and particularly illustrating an energizing transducer adapted to generate a cold plasma;

FIG. 30 is a pictorial view of another embodiment, having an energizing transducer adapted to modify particulate size of treatment agent that is applied to a surface.

DETAILED DESCRIPTION OF THE ILLUSTRATED EMBODIMENTS

Certain preferred embodiments are structured to apply Hydroxyl radicals to a surface for purpose of disinfection, deodorization, and/or sterilization of that surface. One embodiment according to certain principles of the invention may be characterized as a Fenton cleaning wipe. Desirably, a cleaning wipe is a low-cost element, and can therefore be discarded after a single use. Typically, a wipe is structured for activation at the time of use to generate one or more treatment agent at the location of use of the wipe to treat an object.

An exemplary Fenton cleaning wipe includes two or more reactive chemical electrodes, which may be carried by a body formed from flexible polymeric or cellulosic material. A workable body may be structured as a flexible membrane made from e.g., paper, cloth, sponge, sponge-like materials, and the like. The chemicals may be carried on the body, embedded in the body, or carried in one or more pockets formed in the body, or the like. Typically, the electrodes are separated from each other in some fashion, such as by a space, gap, or divider formed by sufficiently inert material. Sometimes, one electrode is carried on the body, and a mating pair element to that electrode is applied by an applicator. When activated (e.g., by moisture such as tap water, or a reactive fluid), the electrodes react with each other and generate a cleaning solution that can be applied to a surface or object. Depending on the amount of reactive chemicals present, the wipe can be used for deodorization, disinfection or sterilization. Sometimes, a wipe may include abrasive materials to facilitate deeper cleaning of a surface or object.

Figure 1:
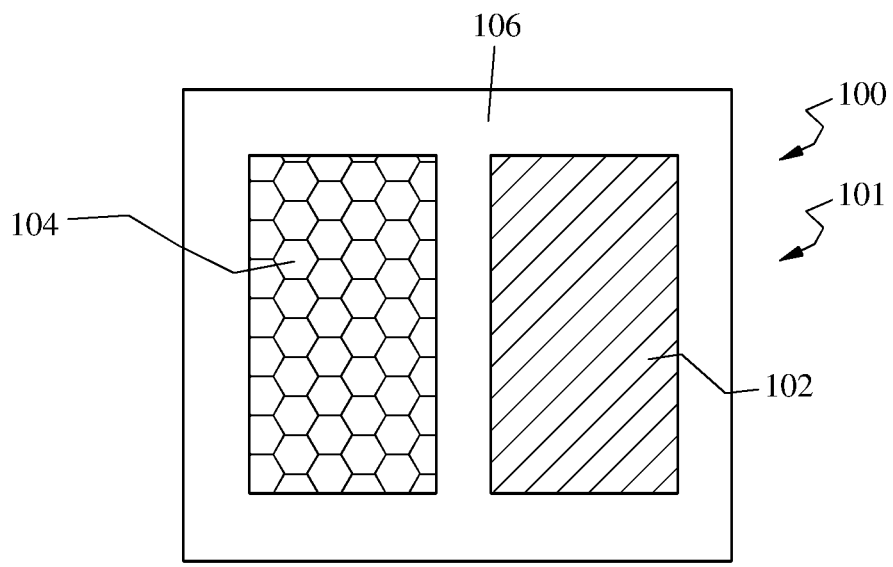
FIG. 1 is a pictorial view in elevation of a first disposable treatment wiper structured according to certain principles of the instant invention.

An exemplary treatment wipe, generally 100, is illustrated in FIG. 1. The treatment wipe 100 in FIG. 1 is a two-electrode embodiment, generally 101, and includes first electrode 102 and second electrode 104 carried by a body 106. First electrode 102 may include a percarbonate compound, such as any alkali-percarbonate. Second electrode 104 may include a Fenton catalyst, such as Iron sulfate ($FeSO_4$) or Iron sulfite ($FeSO_3$). Either one or both of electrodes 102, 104 may be essentially painted-on, or somehow printed-onto or adhered to, body 106. It is alternatively within contemplation that the electrodes 102, 104 can variously be embedded into, or carried in compartments formed in, the body 106.

A body 106 may be formed as a single or multi-layer structure. In the latter case, one side or layer may be structured to provide a barrier (such as a moisture, or chemically-resistant, barrier) between a user's hand and the reactive compounds to be applied to a surface. The other side may be structured to facilitate communication of water or reactive fluid between the electrodes 102, 104, and/or application of one or more treatment agent onto the object to be treated. One or more pocket may be formed between layers in which to hold substances that may form treatment agents.

A treatment wipe 100 may include a variety of different electrode pairs or reactive chemical couples. For non-limiting examples, pairs of electrodes may include: Sodium Chlorate and Citric acid; Citric acid and Silver Citrate; Alkali-Percarbonate and Magnesium Oxide; Sodium Chlorite and Citric acid; Quaternary Ammonium Salt and Calcium Hypochlorite; Alkali-perchlorate and UV light; Silver Chloride and UV light; Iron Sulfate and Alkali-percarbonate; stable Hydrogen Peroxide and Iron Sulfate; Hydrogen Peroxide and Silver Nitrate; Hydrogen Peroxide and one or more Alcohol such as Benzyl alcohol, Methyl alcohol, Ethyl alcohol, and the like; a biocidal conducting electrode with a positive electrical charge dispenser; a biocidal conducting electrode with a negative electrical charge dispenser; and a pair of biocidal conducting electrodes with cooperating positive and negative electrical charge dispensers to simultaneously attract and kill both gram positive and gram negative bacteria or microbes.

Activation of a chemical reaction to produce a treatment reaction product or agent (e.g. a biocidal disinfecting or sterilizing agent) is typically accomplished at the time of a treatment. Wipes may be stored in a substantially inert form, and activated just before, or during, use to treat an object. Activation may sometimes be accomplished by application of a fluid to the dry electrodes 102, 104. Operable fluids can include tap water or sometimes a fluidized chemical reagent. Certain embodiments may include, or otherwise be associated with, an optional UV light or chemical element such as Ozone. Further, one or more abrasive material may be applied to, or included with, one or more of the electrodes 102, 104. It is within contemplation to include a catalyst to promote reaction speed for the resulting chemical reaction of the above-listed and alternative operational pairings or couples. It is further within contemplation to include one or more additional agent to enhance biocidal activity of an electrode 102 or 104. For example, Triclosan may be included in any one of the electrodes.

Figure 2:
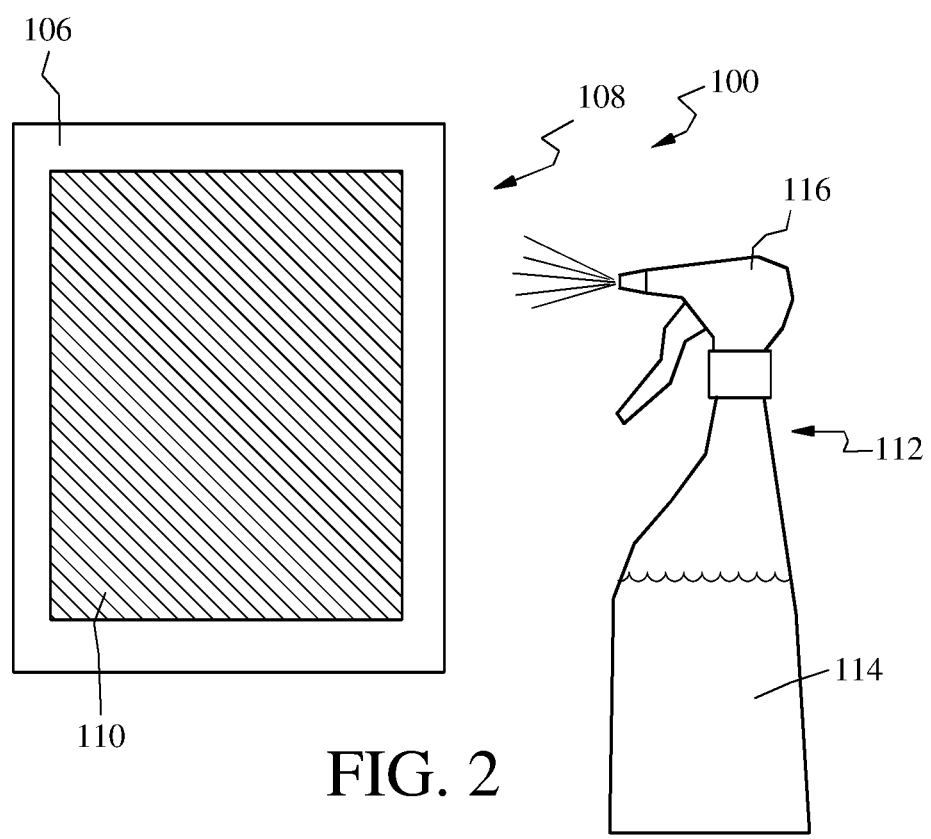
FIG. 2 is a pictorial view in elevation of a second disposable wiper, in combination with a spray bottle of solution.

Alternative embodiments of a wipe 100 may include a single dry electrode including one electrode of the above-listed electrode pairs, and a fluidized activation agent including a mating chemical electrode compound to the dry electrode. The wipe 100 illustrated in FIG. 2 is exemplary of such a single-electrode wipe, generally indicated at 108. Wipe 108 has a single electrode 110 carried on wipe body 106.

A fluid source, generally 112, carries a cooperating reactive substance 114 to generate a treatment agent (which may include biocidal compounds, such as Hydroxyl radicals), when combined with electrode 110. A workable fluid source 112 includes spray bottle 116. For example, if the electrode 110 includes an alkali-percarbonate, a cooperating fluid substance 114 may be a Fenton catalyst in solution, such as Iron Sulfate. In a different case, the single electrode wipe 108 may carry a dry citric acid while the spray device 112 may apply a Sodium Chlorite solution onto the wipe 108 at the time and point of use to create a biocidal Chlorine dioxide compound for deodorization, disinfection, and/or sterilization of an object.

It should be understood that a wipe 100, 101, 108 is typically used as a device operable to spread or apply one or more treatment agent onto the surface of an object. Part of a wipe 100 may apply a fluid to an object to be treated, and another part of the wipe 100 may absorb the fluid along with undesired elements.

Figure 3:
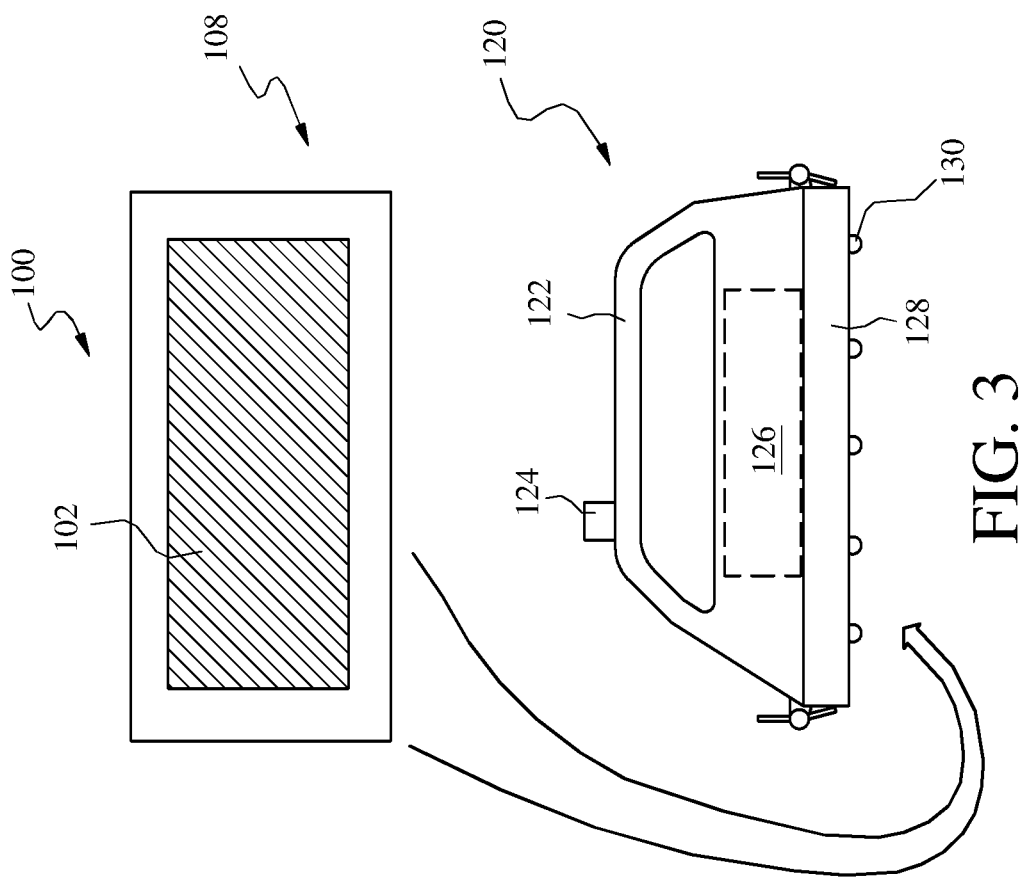
FIG. 3 is a pictorial view in elevation of a third disposable wipe, in combination with a Hydroxyl radical-generating wipe-holder.
Figure 12:
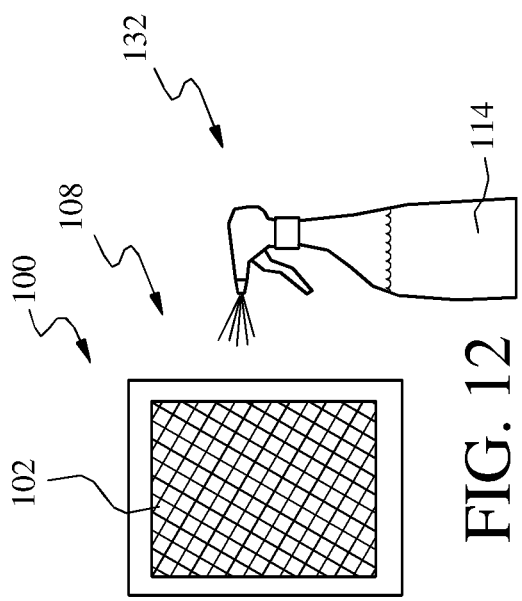

As indicated in FIG. 3, a disposable wipe 100, such as the one-electrode wipe 108, may be carried by a re-usable wipe-holder, generally indicated at 120. The one-electrode wipe 108 may be considered as a disposable cleaning element, somewhat like a commercially available "Swiffer Sweeper"™, but more aggressive in that the wipe 108 can also disinfect and/or sterilize a surface. A workable wipe holder 120 may simply stretch the wipe 108 into a planar, or any other desired, shape. Another operable wipe-holder 120 may include a spray device to introduce moisture (including tap water) or a reactive element to interact with one or more compound carried by a wipe 108.

The wipe-holder 120 illustrated in FIG. 3 includes a short horizontal handle 122 structured to hold in a user's hand, like an iron. It is within contemplation that a handle 122 may be configured for any particular use. For example, an alternative handle 122 may be embodied as an elongate shaft, like a broomstick or mop handle.

The illustrated wipe-holder 120 also includes a switch 124 that couples a power source, such as batteries 126, to operate a UV light 128. In combination with an exemplary wipe 108 that carries e.g. Sodium- (or other Alkali-) percarbonate or perborate, the holder 120 can generate Hydroxyl radicals to deodorize, disinfect, and/or sterilize a surface or object. A fluid source may also be included in a holder 120 to introduce moisture or a reactive element to a wipe 108. Sometimes, a wipe holder 120 may include one or more catalyst 130. Currently preferred catalyst materials include Nano Titanium Oxide and Nano Gallium Nitride wires or tubes.

An alternative holder 120 for a wipe 100 may include a surface corona discharge unit for UV generation, and/or ozone generation. A further alternative holder 120 may generate Ozone. The Ozone generator provides and directs Ozone to react with a chemical compound carried by a wipe 100, which in turn, generates disinfecting or sterilizing fluid in the wipe. Another alternative holder 120 within contemplation generates high temperature steam, which may be applied to either or both of the wipe 100 and surface to be treated. A still further alternative holder 120 may dispense an Iron-based catalyst to interact with a chemical compound carried on a disposable wipe 100. A Fenton reaction may thereby be created in the wipe 100 to produce Hydroxyl radicals for treatment of the desired surface or object.

Another alternative holder 120 for a wipe 100 includes an electrical charge delivery capability to a wipe 100 that is coated with electrical conducting materials, including metals and nonmetals. One operable embodiment 100 can be coated with carbon, or carbon paper may form the wipe itself. Most microbial cells and biological surfaces are negatively charged. In a fluid environment, a positively charged wipe 100 attracts negatively charged bacteria and microbes, and vice versa. If the wipe 100 contains a biocidal chemical, then attracted or otherwise-encountered bacteria or microbes will be killed. For example, if a treatment wipe 100 has a biocidal agent (such as Silver citrate; Sodium Chlorate or Sodium Cholite; Alkali percarbonate; or Sodium dichloroisocynurate) disposed in an electrically conductive electrode, then putting an electric charge on such a wipe will attract and kill oppositely charged bacteria or microbes at, or sufficiently near to, that electrode. In alternative arrangements, simply scrubbing or rubbing a surface with a disposable wipe 100 may cause same-charge bacteria or microbes to encounter the killing zone associated with a biocidal agent and its electrode, or the wipe 100, itself.

Figure 4:
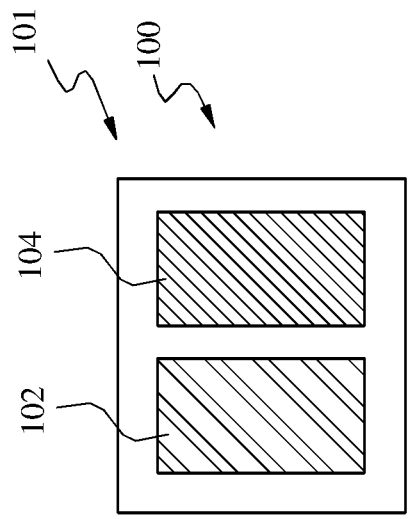
FIG. 4 is a pictorial view in elevation of a fourth disposable wipe.
Figure 5:
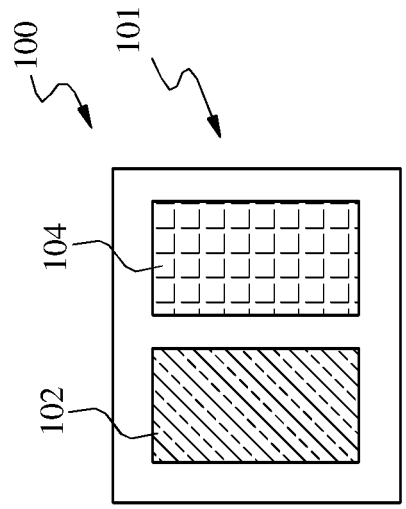
FIG. 5 is a pictorial view in elevation of a fifth disposable wipe.

FIGS. 4-8 illustrate a variety of workable configurations for a disposable wipe 100. Typically, the electrode(s) is/are imparted a sufficient amount of fluid, such as tap water or other activation agent, to initiate a reaction to form an active ingredient that can deodorize, disinfect, and/or sterilize a surface or object. The two-electrode wipe 101 in FIG. 4 illustrates the case when first electrode 102 includes a percarbonate, and second electrode 104 includes Magnesium oxide ($MgO_2$). The two-electrode wipe 101 in FIG. 5 illustrates the case when first electrode 102 includes a percarbonate (such as Sodium percarbonate), and second electrode 104 includes Citric acid, which can sometimes be essentially painted onto the wipe 100. FIG. 6 illustrates the case when first electrode 102 includes Citric acid, and second electrode 104 includes Silver Citrate.

FIG. 7 illustrates the case when first electrode 102 includes Sodium Chlorite, and second electrode 104 includes Citric acid. Again, the electrodes may be painted onto the wipe 100, and then dried for storage and transportation to a site of use. Upon wetting, the electrodes of wipe 100 in FIG. 7 combine to form Sodium Citrate plus Chlorous acid ($HClO_2$). FIG. 8 illustrates first electrode 102 including Sodium Chlorate, and second electrode 104 includes Citric acid. Upon wetting, the two electrodes of wipe 100 in FIG. 8 combine to form Sodium Chlorate ($NaClO_3$).

Figure 11:
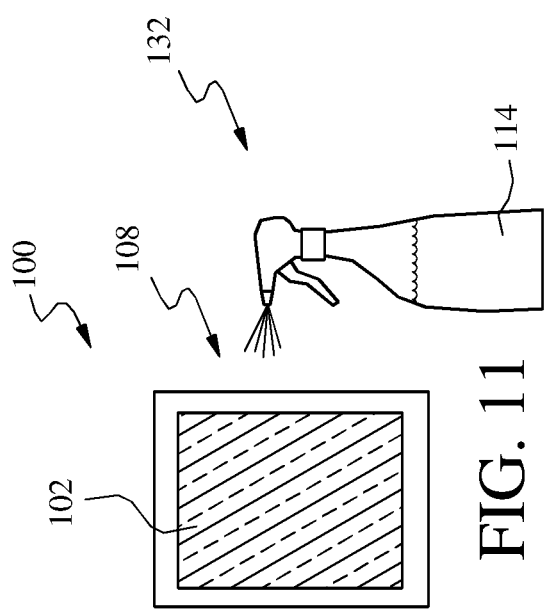
Figure 10:
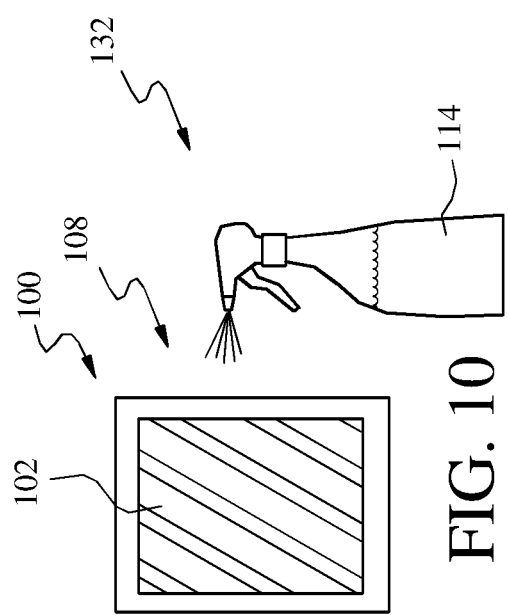

The single-electrode embodiments 108 in FIGS. 9-12 illustrate workable combinations of a disposable treatment wipe 100 that carries one or more chemical compound, and a fluidized activation agent, generally 132, that is combined with the wipe 100. In FIG. 9, electrode 102 may be made from, or include, Citric Acid that is painted, or otherwise applied to the single-electrode wipe 108, and then dried. A cooperating fluidized substance 114 may include: Sodium Chlorite; Sodium Chlorate; Calcium Chlorate; and/or Calcium Chlorite. Electrode 102 in FIG. 10 may similarly be, or include, Citric Acid, and activation substance 114 may be an Alcali-Percarbonate. FIG. 11 illustrates the reverse situation, where electrode 102 may be, or include, an Alcali-Perchlorate, and activation substance 114 includes Citric acid. Electrode 102 in FIG. 12 may be, or include, Calcium hypochlorite, and cooperating activation substance 114 may include an Iron (II) Sulfate solution ($FeSO_4$).

In certain other embodiments within contemplation, a fluid source may include two or more chemical compounds that are separately stored, but when sprayed together onto a wipe (or directly onto a surface), generate a biocidal substance effective to disinfect and/or sterilize a surface. In that case, an operable wipe 100 may be embodied as a commercially available paper towel, or the like. An operable fluid source includes a pair of spray bottles 116 (FIG. 2), or a single spray bottle having two or more containers with provision to dispense two or more chemical compounds simultaneously. A multi-compartment fluid source may be included in a wipe holder, or simply used in conjunction with a disposable wipe 100.

For one example, one container may hold Sodium chlorite and another container may hold Citric acid. When sprayed together onto a wipe 108, Chlorine dioxide is created on the wipe 108, which can then be used to sterilize or disinfect a surface. A further non-limiting example includes a fluid source with one container holding Iron catalyst in solution and Hydrogen peroxide in another container. When sprayed together onto a wipe (or even directly onto a surface), the Fenton reaction generates Hydroxyl radicals to disinfect or sterilize the surface. In another embodiment, a spray bottle with either one compartment or multiple compartments can generate a sterilizing agent from just one chemical or multiple chemicals in different compartments to generate sterilizing agent on demand to sterilize, or otherwise treat, a surface.

Figure 13:
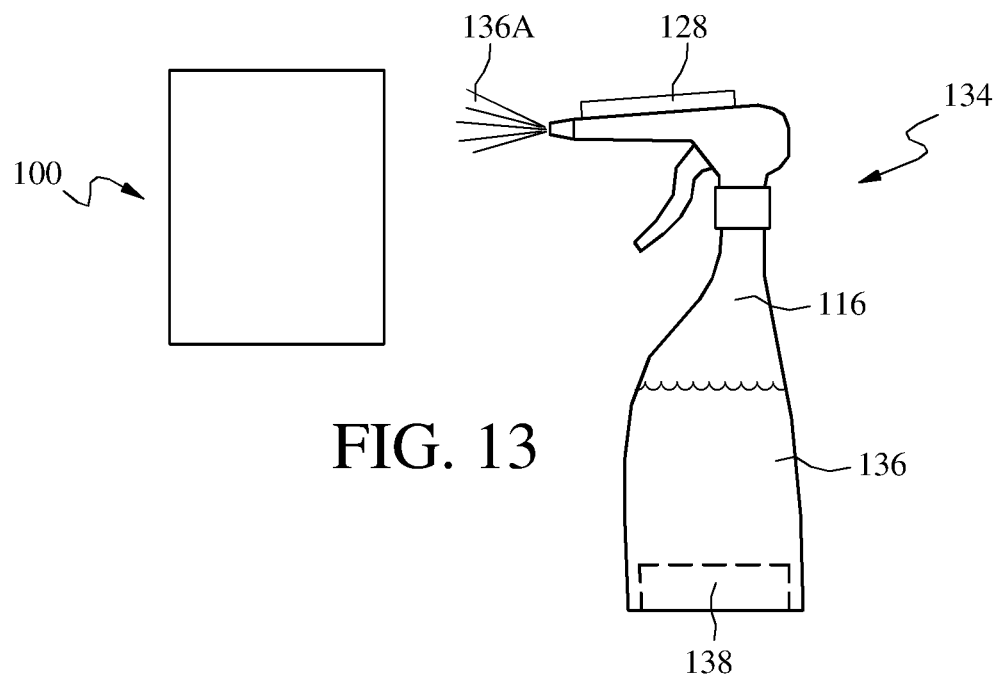
Figure 14:
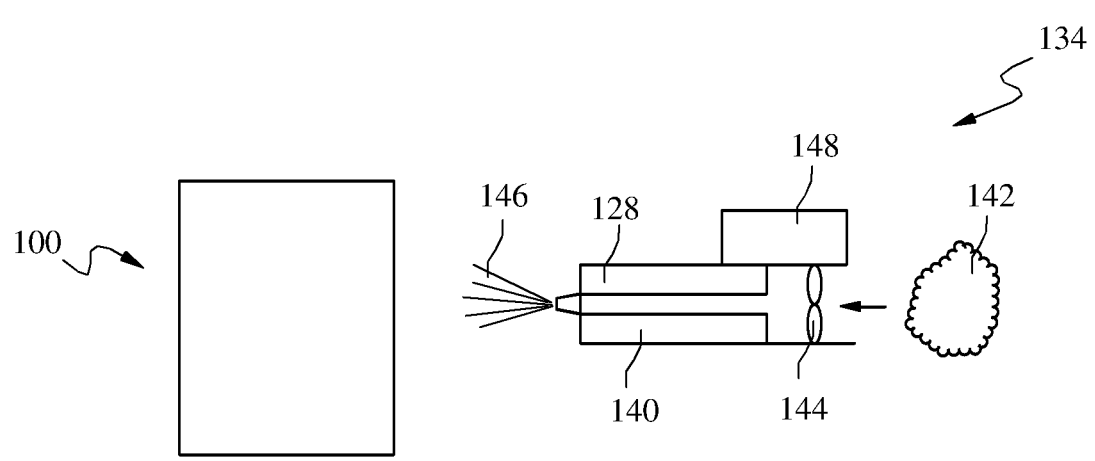
FIG. 14 is a pictorial view in elevation of a disposable wipe in combination with an alternative workable generator of Hydroxyl radicals.

FIGS. 13 and 14 illustrate alternative embodiments, generally 134, that generate a toxic, biocidal, or sterilizing agent on demand. Versions of these embodiments may also include a wipe holder, be incorporated into a wipe holder, or may otherwise be employed in combination with one or more disposable wipe 100. FIG. 13 illustrates a spray bottle 116 adapted to carry a UV light 128 for irradiating a stream of fluid 136 to permit discharge of irradiated fluid 136A to dispose one or more treatment agent on a wipe 100. UV light 128 may conveniently be powered by an on-board power source, such as battery 138, for untethered operation. Other times, UV light 128 may be powered by a conventional cord-and-electric-outlet arrangement. Workable fluids 136 include Hydrogen peroxide ($H_2O_2$) and/or an Alkali-perchlorate solution.

FIG. 14 illustrates another embodiment 134 in which UV light 128 is arranged to impinge onto a treatment agent precursor 140, such as Alkali-percarbonate. Moisture 142 is urged by a device (such as a fan 144, pump, or other device), to flow through the irradiated zone, and produce a treatment agent 146 that is applied to the treatment wipe 100. Elements of a device such as the device 134 in FIG. 14 may be operated, at least in part, by a control module 148. Control module 148 may include an on-board power source, or communicate to a power source.

Figure 15:
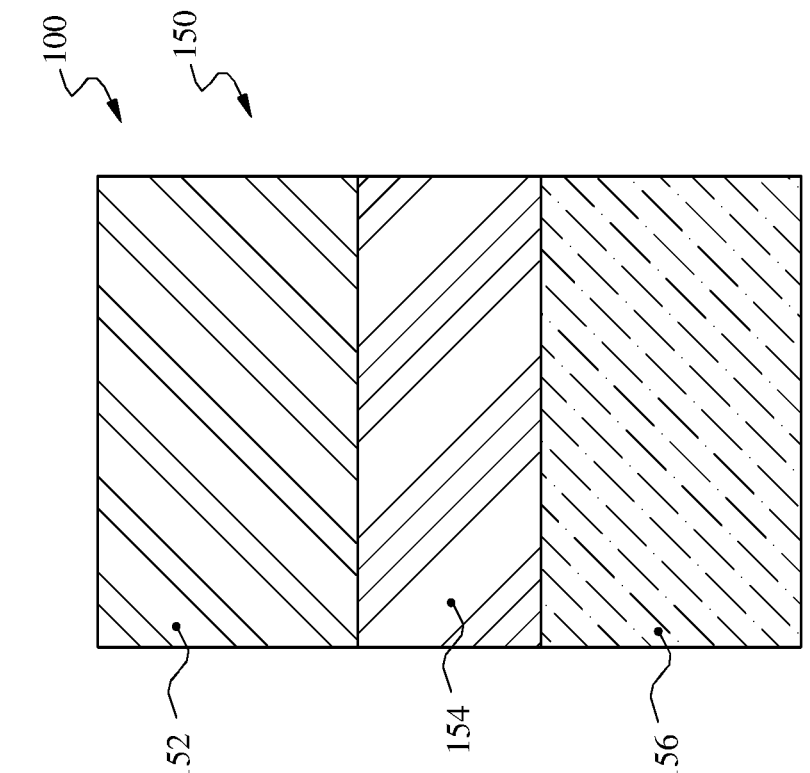
FIG. 15 is a pictorial view of a multi-compartment embodiment of a wipe.

FIG. 15 illustrates a multi-compartment embodiment 150 of a treatment wipe 100, which can be used separately, or in combination with a wipe holder 120. Multi-compartment wipe 150 includes a first compartment 152, second compartment 154, and third compartment 156. A compartment may be defined by dividing walls, or even sometimes by a space disposed between quantities of chemical compounds or electrodes that may be carried in various ways on a wipe 100. In one preferred embodiment 150, compartment 152 carries an Alkali-percarbonate; compartment 154 carries Citric acid; and compartment 156 carries Iron Sulfate ($FeSO_4$).

Figure 16:
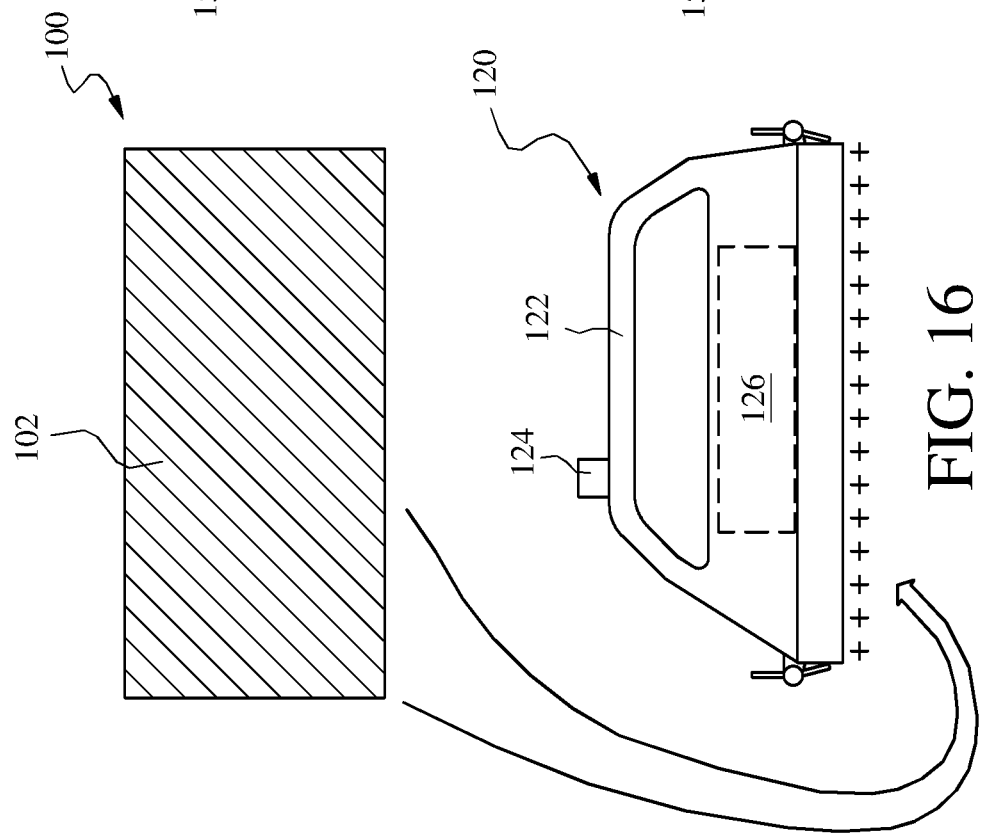
FIG. 16 is a pictorial view of another embodiment including a holder and wipe that incorporates a positive charge dispenser.

FIG. 16 shows another embodiment including a wipe holder 120 and wipe 100, wherein the wipe holder 120 operates as a positive charge dispenser. The wipe 100 illustrated in FIG. 16 includes a biocidal carrying electrode 102 that is activated by the wipe holder 120. The wipe holder 120 illustrated in FIG. 16 can put a positive charge on the wipe to attract gram negative bacteria and microbes. Certain embodiments may be structured such that, subsequently, or alternatively, or even simultaneously, holder 120 may induce a negative charge on the wipe to attract gram positive bacteria or microbes. Once the bacteria or microbes are attracted and contact the wipe, a biocidal agent included in the conductive electrode 102 kills all the bacteria or microbes.

Figure 17:
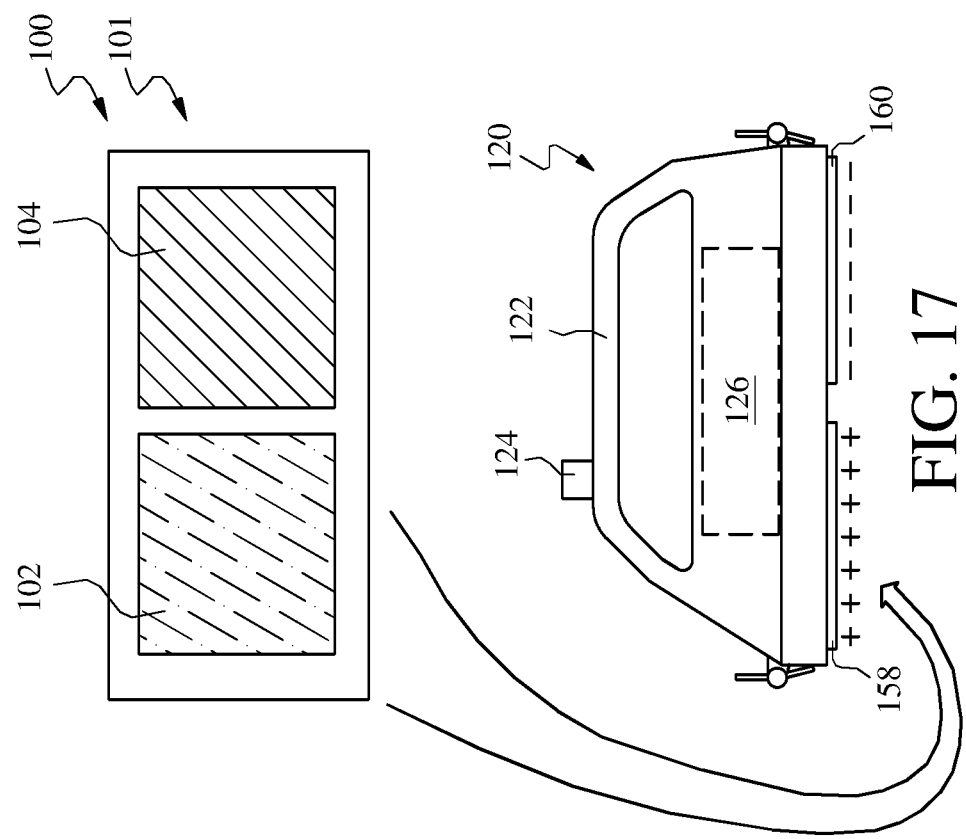
FIG. 17 is a pictorial view of another embodiment including a holder and wipe that incorporates a dual charge dispenser.

FIG. 17 illustrates an embodiment of a wipe holder 120 including both of a positive electrode 158 and a negative electrode 160 to simultaneously apply positive and negative charge to different areas of a wipe 100. The electrodes 102 and 104 of two-electrode wipe 101 in FIG. 17 are electrically conductive, and desirably each includes one or more biocidal agent.

Figure 18:
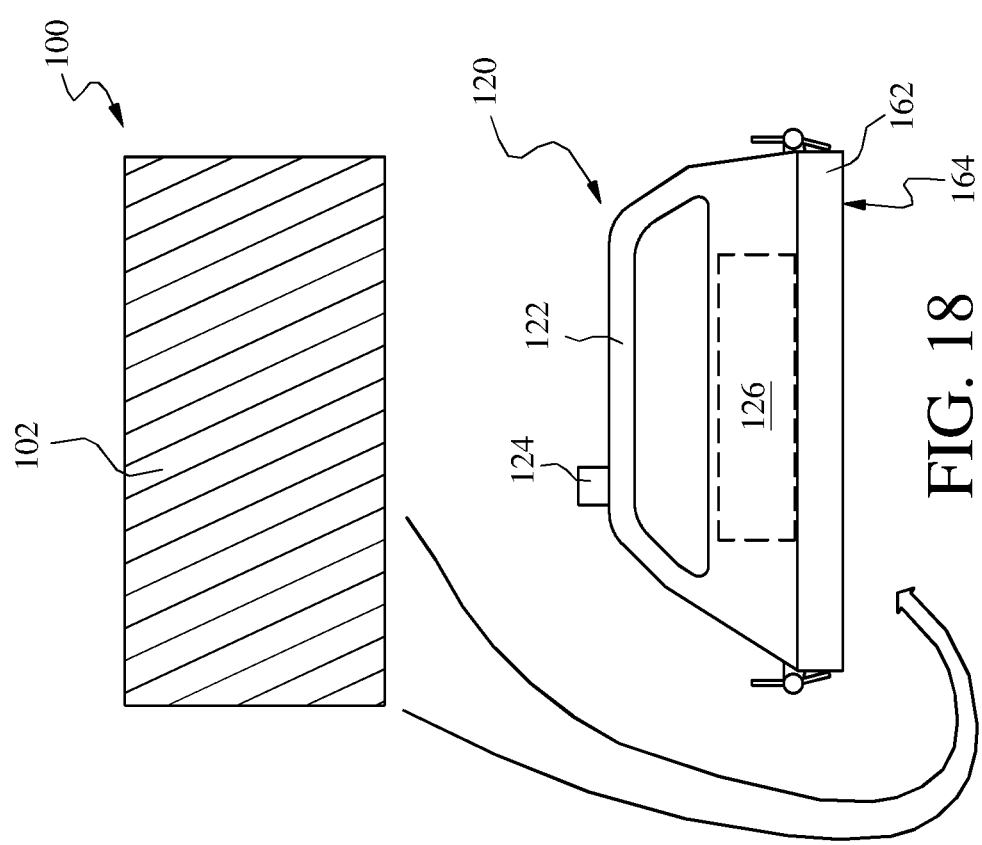
FIG. 18 is a pictorial view of another embodiment including a holder and various wipes that incorporate a thermal element.

FIG. 18 illustrates still another embodiment of a wipe holder 120 and a wipe 100, wherein the wipe holder 120 includes a thermal heating element 162. Desirably, the thermally conductive surface 164 is capable of attaining over 100 degrees Centigrade. A cooperating electrode, such as electrode 102, may include Sodium Chlorite trihydrate, or Sodium Chlorite trihydrate embedded into, or otherwise carried on the wipe 100.

Figure 19:
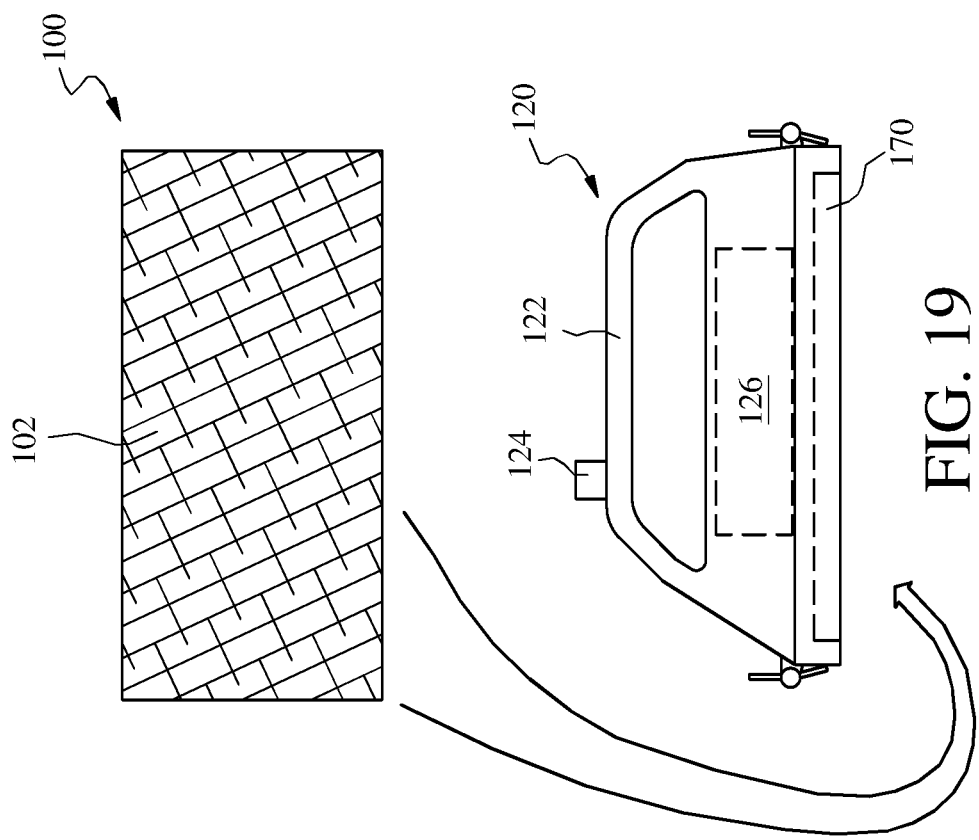
FIG. 19 is a pictorial view of still another embodiment including a holder that incorporates a UV element and a cooperating wipe.

FIG. 19 shows another embodiment including a wipe holder 120 that incorporates a UV lamp element 170 with a cooperating wipe 100. In this arrangement, wipe 100 may carry one or more electrode 102 including Sodium Chlorite. Further, sometimes a catalyst, such as nano-Titanium Oxide ($TiO_2$) or nano-Galium Nitride (GaN) needles, tubes, wires, and the like may also be included to enhance formation of one or more treatment agent(s).

Disposable wipes 100, such as single-electrode wipe 101, or a multi-electrode wipe such as 108 or 150, can be manufactured in a reel-to-reel process. Electrodes, or separate chemical compound elements, may be applied to discrete body portions with a painting-type, or printing-type process as a ribbon of body material passes by. Individual wipes may then be sectioned from the ribbon, stacked, and packaged, as desired.

Figure 20:
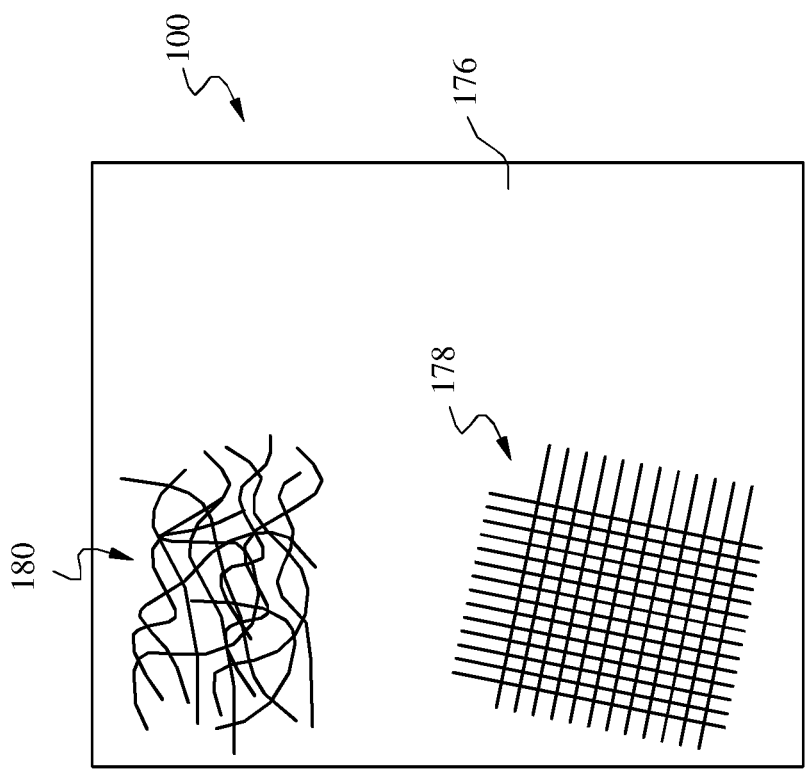
FIG. 20 is a pictorial plan view of another embodiment of a wipe.
Figure 21:
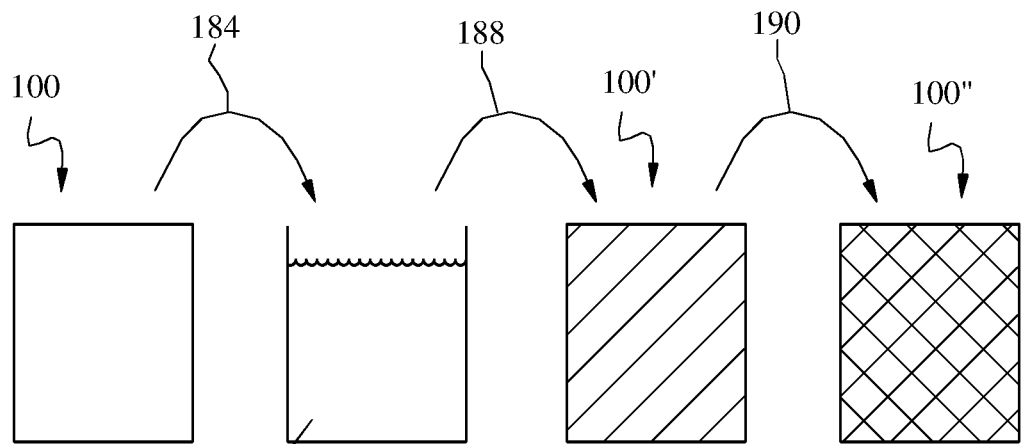
FIG. 21 is a pictorial side view of a workable manufacturing process to make a wipe similar to that illustrated in FIG. 20.

With reference to FIGS. 20 and 21, an alternative embodiment of a disposable treatment wipe can be constructed to generate alcohol when activated by water. With reference to FIG. 20, a treatment wipe 100 of this type provides a framework on which is carried a compound 176 that generates an active cleaning, sterilizing, or deodorizing agent when combined with a second element, such as water or other solvent. A suitable framework can be formed by warp and weave fibers in a woven cloth, generally 178, or random strands, generally 180, arranged to form a membrane or pad, as well as many other substrates that can carry a workable alcohol-producing compound. A workable compound 176 includes a form of dextrin combined with an alcohol to form a substantially dry and solid material.

As with previously-described wipes, the treatment wipe embodiment 100 illustrated in FIG. 20 may be used alone, or in combination with a wipe holder of some sort. It is within contemplation that an embodiment such as illustrated in FIG. 20 may also be used in combination with one or more other type of disposable (or even non-disposable) wipe structured as previously described. Nothing in this description is intended to be limiting.

A solid alcohol treatment wipe 100 of the type illustrated in FIG. 20 may be manufactured in a variety of ways. One workable way includes incorporating a dextrin compound, such as maltodextrin or cyclodextrin, and an alcohol, such as ethyl alcohol, as a composite in the wipe 100. As illustrated, a wipe 100 can be submerged (as indicated by arrow 184) into a solution of a (modifier)dextrin compound 186 or otherwise sufficiently wetted with the solution, removed and dried (as indicated by arrow 188), to form a wipe 100' having (modifier)dextrin (dry) embedded onto the wipe 100'. An alcohol solution is then dispersed (e.g. sprayed) onto the wipe (as indicated by arrow 190) and forms a (modifier) dextrin-Alcohol complex in-situ on the wipe 100". The wipe 100" is then dried (if needed), and can be stored, packaged, etc., prior to use. In use, a fluid such as water may be sprayed onto the wipe 100", or the surface to be cleaned, deodorized, sanitized, disinfected, and/or sterilized, and the compound 176 carried on the treatment wipe 100″ combines with that fluid to generate alcohol for use as a treatment agent.

An alternative embodiment may be manufactured by wetting the wipe substrate (e.g., dipping) in a Sodium Carbonate solution, then drying the impregnated wipe. Subsequently, the wipe can be sprayed, or again appropriately wetted, with a solution of stable Hydrogen Peroxide containing Silver nitrate or Silver Citrate or Benzyl alcohol, or Triclosan, and then dried. Upon activation by fluid, such as water, the resulting wipe will generate and delver disinfectants to an object to be treated and kill microbes on its surface.

Another embodiment within contemplation may be manufactured by wetting a wipe substrate with a concentrated solution of Sodium Carbonate and Magnesium Sulfate, then drying the wipe. Subsequently, a highly concentrated solution of Hydrogen Peroxide containing Silver nitrate can be sprayed or otherwise applied to the wipe. Then the wipe is again dried. Upon activation by a fluid, such as water, the wipe delvers a disinfectant to the surface to be treated.

Figure 22:
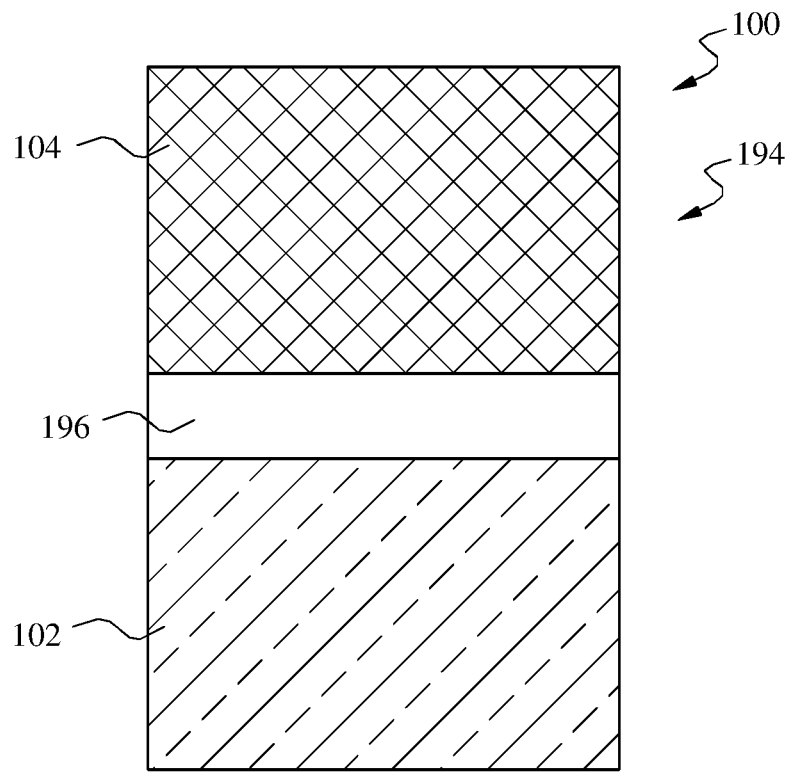
FIG. 22 is a pictorial view of an embodiment with an on-board charge generator.

Embodiments have been disclosed above in which one or more area of electrical charge is/are established by a wipe holder, or an external source of electrical charge. With reference now to FIG. 22, a treatment wipe 100 may be structured to include a battery to provide on-board capability to generate areas of positive and negative electrical charges. The charge-generating treatment wipe embodiment generally indicated at 194 includes first electrode 102 and second electrode 104. Desirably, those electrodes are separated by a divider 196. A workable divider 196 includes a space between compounds that make up the electrodes, or sometimes, a physical wall or barrier. In this case, electrode 102 may be regarded as the anode, and electrode 104 may be regarded as the cathode.

An exemplary anode 102 may include Zinc, a biocidal agent, and Sodium Chloride. An exemplary cooperating cathode 104 may include Silver Chloride, a biocidal agent, Sodium Chloride, and Carbon. Upon activation by a fluid, such as water, Zinc becomes the positive electrode while Silver Chloride becomes the negative electrode. The gram negative microbes will be attracted to the Zinc electrode, and the gram positive microbes will be attracted to the Silver Chloride electrode. Biocidal material contained in the respective electrodes will kill the attracted microbes, as well as be delivered to the surface to be treated. Workable anodes include Zinc, Aluminum, and Magnesium. Workable cathodes include Carbon and Silver Halides. Workable biocidal agents nonexclusively include quaternary ammonium compounds, Triclosan, or other organic biocidal agents.

Figure 23:
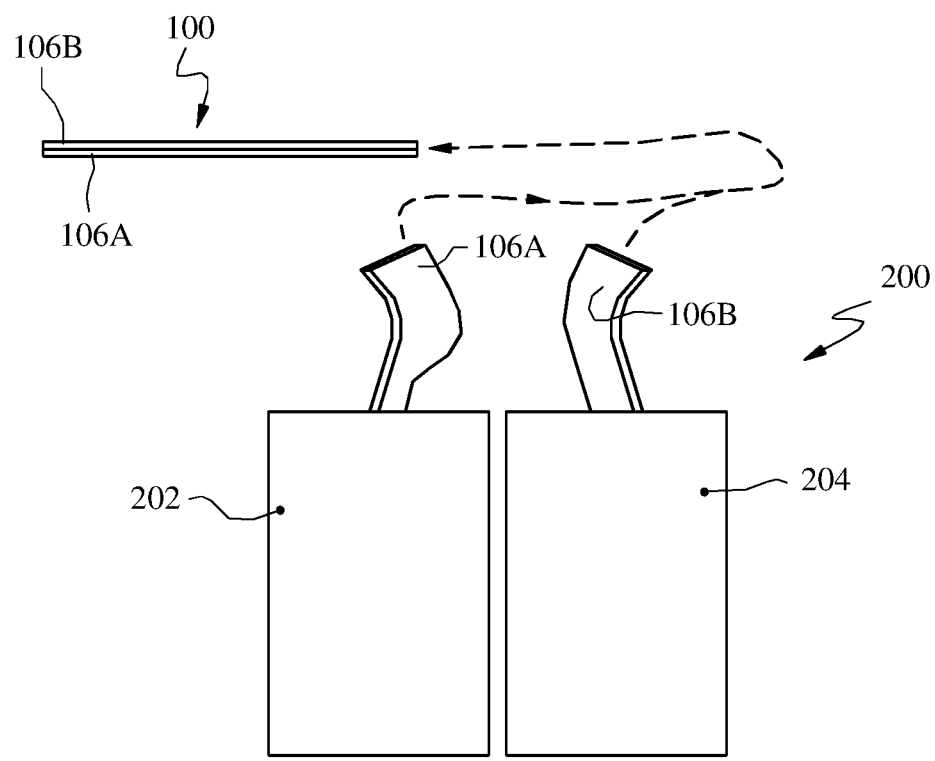
FIGS. 23 and 24 are pictorial views in elevation of wipe embodiments in association with wipe component dispensers.

A treatment wipe 100 may be formed by a combination of a plurality of prepared-in-advance substrates that may be dispensed, combined, and used at the location and time of treatment of an object. With reference to FIG. 23, wipe 100 is formed by combining a first substrate 106A with a cooperatingly structured second substrate 106B.

Figure 24:
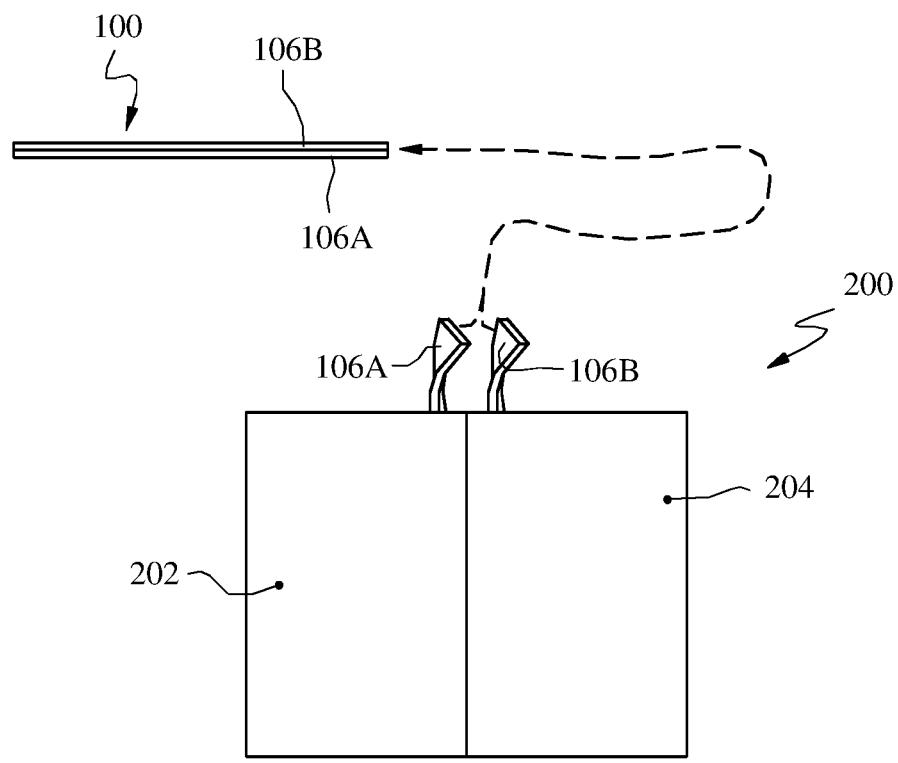

A convenient dispenser for cooperating substrates, generally 200, provides a first compartment or chamber 202 and a second compartment or chamber 204. Individual compartments may be separate elements, or, connected together in a unitary structure. The dispenser 200 in FIG. 24 is structured in such a way that substrates 106A and 106B are simultaneously dispensed and combined for use. Compartments desirably are each structured to contain a plurality of substrates. Sometimes substrates are stored in a dry, or near-dry condition. Other times, substrates may be moist or wet. Therefore certain compartments 202, 204 are structured to confine moisture or even to hold excess or freestanding liquid.

In accordance with the foregoing disclosure, it should be realized that first compartment 202 may contain substrates 106A that individually carry one or more of: Hydrogen Peroxide, Sodium Chlorite, Sodium Chlorate, and/or Quaternary Ammonium salt. In further harmony with the above disclosure, second chamber 204 may confine substrates 106B that individually carry on or more of Silver nitrate, Silver Citrate, Citric acid, any mild acid, solid acid, and Iron Sulfate.

In one exemplary embodiment 200, chamber 202 holds a plurality of substrates 106A that carry Hydrogen Peroxide, and chamber 204 holds substrates 106B that carry Iron Sulfate solution. When combined, the compounds carried on the substrates form a wipe 100 that produces Hydroxyl radicals as a treatment agent that may be applied to an object to deodorize, disinfect, and/or sterilize the object.

Figure 26:
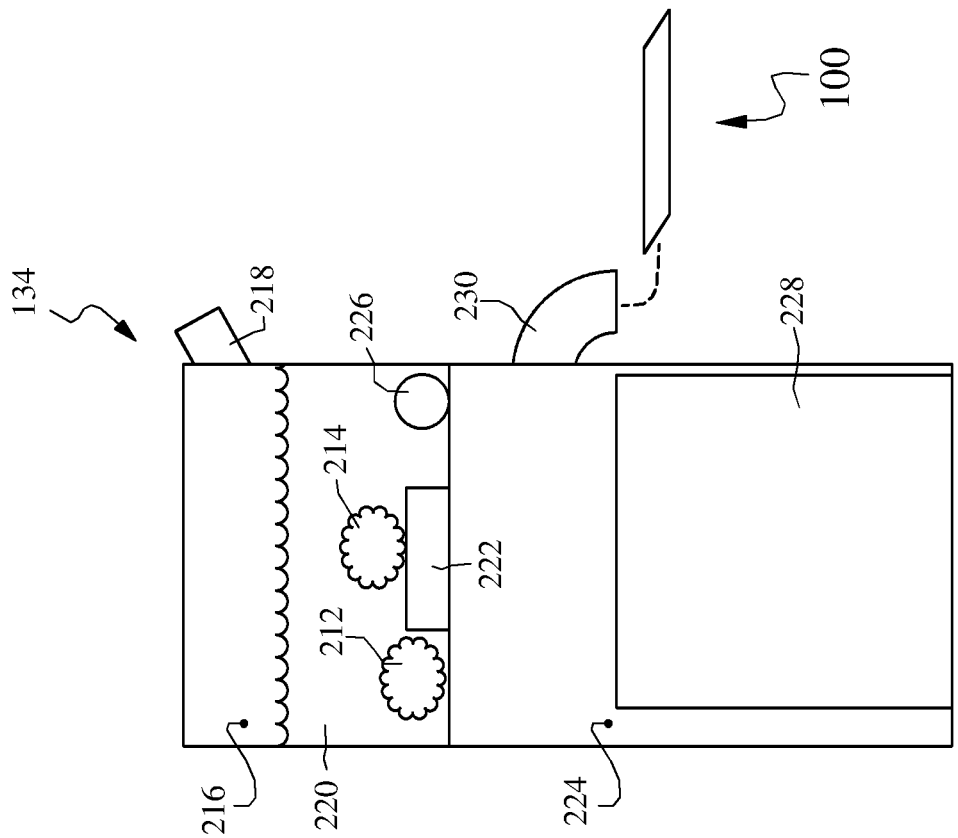
FIG. 26 is a second pictorial view in elevation of an applicator of treatment agent to a plurality of wipes.
Figure 25:
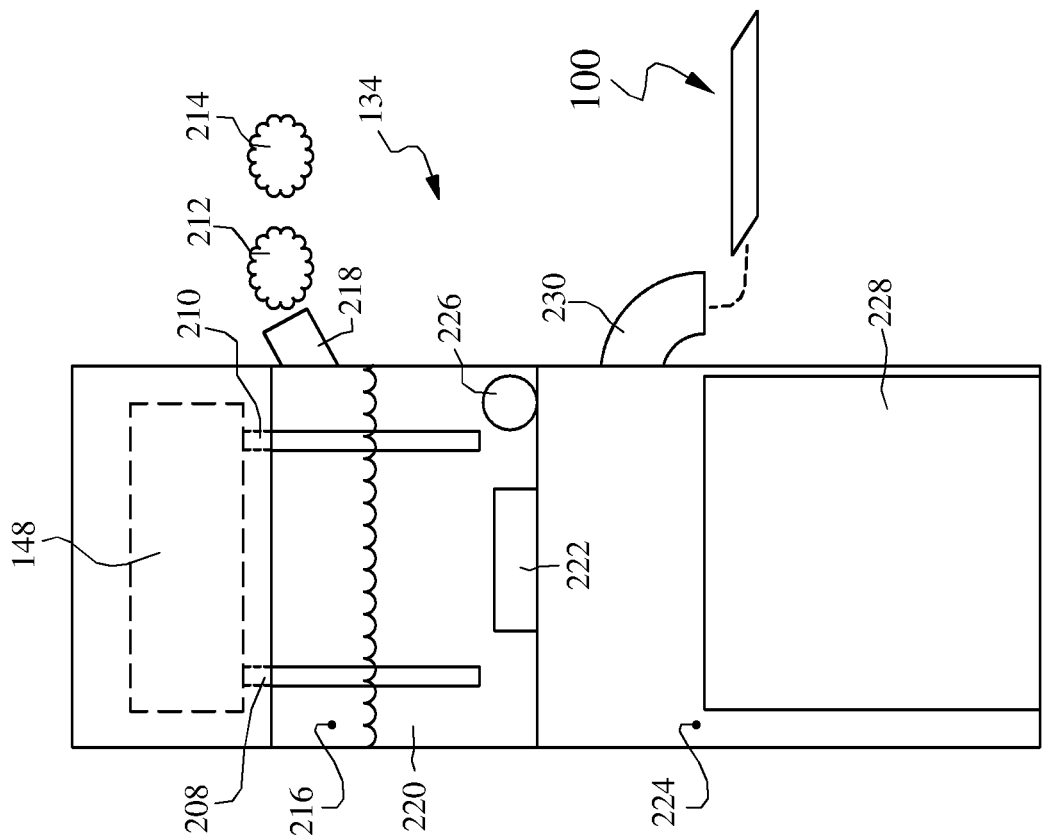
FIG. 25 is a first pictorial view in elevation of an applicator of treatment agent to a plurality of wipes.

Embodiments according to certain principles of the invention may be structured to generate one or more treatment agent on demand, and apply the product(s) to a wipe substrate or body 106. Some examples are illustrated in FIGS. 13 and 14. Additional such embodiments 134 are illustrated in FIGS. 25 and 26. In FIG. 25, treatment applicator 134 includes a first electrode 208 configured as a cathode. A second electrode 210 is configured as an anode. Precursor elements 212 and 214 (which may be salt and water, respectively), are added to upper chamber 216 through a sealable door 218. A control module 148 energizes the electrodes 208 and 210, to produce one or more treatment agent from precursor elements 212, 214. The device 134 may be embodied as a cordless, or corded appliance. Typically, the device 134 is sized on the scale of a 2-slice toaster. An advantage of the device 134 in FIG. 25 is that it may be transported and sold without requiring the additional weight of water, which is supplied buy a consumer at the location of wipe creation.

When the precursor elements include salt and water, the device 134 produces a treatment solution 220 including Sodium hypochlorite. That solution may be applied through a re-sealable aperture 222 to a plurality of wipe bodies 106 that are stored in lower compartment or chamber 224. A re-sealable aperture 222 may be embodied in many forms, including a guillotine valve, for example. Sometimes a stabilizer 226 may be included in the treatment solution. A door or opening 228 permits adding dry wipe bodies 106 to chamber 224. Desirably, a mechanism is provided to facilitate removal of a desired number of prepared wipes 100. One such device includes wipe dispensing spout or chute 230. It is within contemplation that chamber 216 may communicate through a metering device to dispense an appropriate amount of treatment fluid to one or more wipe 100 at a time.

The treatment agent applicator 134 illustrated in FIG. 26 is similar in certain respects to the embodiment in FIG. 25, and is numbered accordingly. Applicator 134 in FIG. 26 is particularly structured to permit chemical reaction of a plurality of precursor compounds (e.g. 212, 214) to generate Hydroxyl radicals in top chamber 216 upon addition of water to react with compounds 212, 214. Compounds 212, 214 may be selected from couples disclosed above, and include Sodium percarbonate and Silver Nitrate; Magnesium Sulfate and Iron sulfate; Sodium percarbonate and ozone generator; Sodium percarbonate and UV light; catalyst and UV light; Hydrogen peroxide and Iron Sulfate or UV light or ozone generator.

The embodiment 134 in FIG. 26 may alternatively be operated to generate disinfecting chemicals or treatment agents. Operable couples in that case nonexclusively include: Silver halides and UV light; Silver citrate and citric acid; Sodium chlorate or Sodium chlorite and citric acid or other mild acid; Quaternary Ammonium salt, with or without Silver halides or citrates or Nitrates; and Ozone generator.

Exemplary Test Data

A wipe was made by printing two carbon electrodes onto a substrate, which was then saturated with Sodium Chloride. A prototype wipe holder with a battery powered the electrodes to form Sodium Hypochlorite as a treatment agent. Test data for treatment of a stainless steel surface on a coupon contaminated with *E. coli* resulted from following the protocols set forth below:
Application Method 1=2 squirts of tap water on coupon surface, 2 squirts on prototype pad, turn on prototype for 20 sec, wipe surface 3 times, allow sample to sit for 10 min, and analyze sample.
Application Method 2=2 squirts of tap water on coupon surface, 3 squirts on prototype pad, turn on prototype for 30 sec, wipe surface 4 times, allow sample to sit for 10 min, and analyze sample.

In either case, the percent reduction of *E. coli* ACC 8739 was >99.981 percent.

With reference now to FIGS. 27 and 28, a holder 120 for a wipe may be embodied as a mitt, mitten, or glove 240. Mitt 240 constitutes a housing that provides conventional enveloping structure into which a user's hand may be inserted to manipulate the mitt during deodorizing, disinfecting, and/or sterilizing a surface. Other workable housings and alternative structures may be envisioned to provide structure arranged to receive a human hand to manipulate a holder 120 during deodorizing, disinfecting, and/or sterilizing a surface.

The housing provided by illustrated mitt 240 carries a plurality of energizing transducers, generally 242. Energizing transducers 242 associated with a housing or holder may all be the same, or they may include an assortment of different transducers. A workable transducer 242 is operable to modify a treatment agent, or to create a treatment agent, or sometimes, both. Workable energizing transducers 242 nonexclusively include: electrical field such as cold plasma generator, UV light, ion generator, and fluid particle size-modifying. A plurality of cold plasma generating transducers 244 are particularly illustrated in e.g., FIG. 27.

Desirably, a fluid particle size-modifying transducer is operable to create micro-, micron-, or nano-sized particles of a treatment agent. A particle size-modifying transducer, or nebulizer, may be embodied in various forms, including ultrasonic, electrical (e.g., piezo), mechanical, such as on a pressurized fluid source (e.g., fluid atomizer with a large pressure differential across a small aperture and a strong spin being imparted to the exiting fluid), and thermal fogger.

It is typically desirable to provide a portable power source (e.g., a battery pack and control system 246) in operable association with a wipe holder, such as the mitt 240, to facilitate deodorizing, disinfecting, and/or sterilizing a surface with the device. Wires or control leads, generally 248, permit placement of the power/control system 246 at a convenient location. Exemplary convenient locations include the back of a mitt 240, or on the belt of an operator. A heavier battery pack may be carried in a backpack worn by an operator, or even placed on the floor in the vicinity of an object to be treated. However, it is within contemplation that a wipe holder 120 may also be structured for tethered operation to a conventional plug-in electrical outlet.

With reference to FIG. 28, mitt 240 constitutes an element of an applicator of energized treatment agent, generally indicated at 250. By "energized" it is intended to mean that the applicator 250 is structured to apply a modified and energized form of a treatment agent, or an alternative energized treatment agent derived from or made from an original treatment agent, which energized form has an enhanced power to kill microbes, when compared to the original treatment agent.

The applicator 250 illustrated in FIG. 28 includes a holder 120 (the mitt 240) and a wipe 100. Illustrated wipe 100 is structured as an over-mitt 252, inside of which mitt 240 can be inserted. Over-mitt 252 may be installed in operable position in registration with a holder 240 like a sock onto a foot or a mitten onto a hand. A wipe operable with a holder 240 may be embodied in alternative shapes, nonexclusively including a rectangular bag or open-ended cylinder. Wipe 252 may be structured as a disposable membrane-like element according to previously described wipes. However, a preferred wipe 252 carries a fluidized treatment agent, such as Hydrogen peroxide in a range of about 2% to about 30%.

In certain embodiments, such as when over-mitt 252 carries a fluidized treatment agent, for example Hydrogen Peroxide, and a transducer 242 is embodied as a nebulizer to convert the Hydrogen Peroxide into micron- or nano-sized particles, the system illustrated in FIG. 28 applies energized treatment agent as a fog onto a treatment site or surface, and the energized treatment agent is wiped by the over-mitt 252. Sometimes, a plain wipe 100 (e.g., a dry paper towel, or cloth) may also be used, in combination with an embodiment such as illustrated in FIG. 28 and particularly described here, to remove residual treatment agent from the surface.

A preferred mitt 240 provides a holder 120 for a wipe 100 (see FIGS. 27 and 28) that is compliant and permits application to, and contact of a wipe 100 with, an irregular, non-flat, or curved surface. A user's hand may deform the wipe 100 to cause a desired conformation of a disposable wipe 100 to the surface to be treated.

A mitt 240 may be structured to be reusable. An exterior surface 254 may be treated, e.g., rubberized, to permit cleaning the mitt for reuse with a plurality of successive disposable wipes 100.

FIG. 29 illustrates a wipe 100 in combination with a holder 120 that is particularly structured to impart cold plasma to the wipe. The wipe 100 may be associated with the holder 120 by affixing opposite ends of the wipe 100 to clamps 258. Wipe holder 120 in FIG. 29 includes a cold plasma generator/transducer 244, arranged to impart plasma to a wipe 100 at a wipe-support surface 262. The embodiment 250 in FIG. 29 may be regarded as a fairly rigid embodiment, although a compliant surface 262 is within contemplation in alternative embodiments. The plasma generator 244 transforms and "energizes" a portion of a treatment agent, such as Hydrogen Peroxide carried on a wipe 100, into Hydroxyl radicals, thereby energizing the treatment agent.

Various types of cold plasma generators 244 may be employed in embodiments of the invention. Operable cold plasma transducers of various types including Dielectric barrier discharges (DBD), resistive barrier discharges (RBD), cascaded dielectric barrier discharge (CDBD), corona plasma discharges (CPD), and the Atmospheric Pressure Plasma Jet (APPJ) or the plasma plume, are disclosed in "Plasma Based Sterilization: Overview and the Stepwise Inactivation Process of Microbial by Non-thermal Atmospheric Pressure Plasma Jet", by M. R. Pervez, A. Begum, and M Laroussi, in the International Journal of Engineering & Technology IJET-IJENS Vol: 14 No: 05. The disclosure set forth in this paper is incorporated by this reference, as though set forth herein in its entirety.

An analysis of Surface Micro-Discharge plasma effect on microorganisms is presented in the Dissertaion titled SURFACE MICRO-DISCHARGE (SMD)—ANALYSIS OF THE ANTIMICROBIAL EFFECT AND THE PLASMA CHEMISTRY, by Jin Jeon, geboren am 27 Sep. 1984 in Seoul/Südkorea. A similar analysis is set forth in "Cold Atmospheric Air Plasma Sterilization against Spores and Other Microorganisms of Clinical Interest", by Tobias G. Klampfl, Georg Isbary, Tetsuji Shimizu, Yang-Fang Li, Julia L. Zimmermann, Wilhelm Stolz, Jurgen Schlegel, Gregor E. Morfill, and Hans-Ulrich Schmidt, in Appl Environ Microbiol., 2012 August; 78(15): 5077-5082. The disclosures set forth in these papers are also incorporated by this reference, as though set forth herein in their entirety.

Disinfection Testing of Commercially Available $H_2O_2$ Wipes

Procedure: *Geobacillus stearothermophilus* spores were procured from Croostex®. Tryptic Soy Broth was prepared in the lab as the growth media. The *Geobacillus* spores had a population of $1.5 \times 10^6$. Positive and negative controls were prepared to observe the growth and for comparison. The test procedure was as follows:
1. Place the spore plate on a clean and sterile surface facing upwards
2. Place the disinfecting wipe on top such that it contacts the spores
3. Wait for a specific time limit and then remove the wipe
4. Pick the spore plate and drop it into the media tube and place in the incubator The positive control was not treated with any disinfecting medium. Two positive controls were prepared, one with no treatment at all and one which was kept in contact with a wet wipe containing only water. In addition to the hydrogen peroxide wipe the spores were treated with a combination of the wipe and Cold Corona Plasma for 1 min, 30 sec and 15 sec. The negative control was prepared by treating the spore plate with 10% bleach for the same time as the wipe.

The treated spore plates were submerged into the media in test tubes which were then placed in an incubator shaker at 55° C. and 250 rpm. Test results are presented in Table 1. $H_2O_2$

TABLE 1

| Description | Time | % kill | Time | % kill | Time | % kill |
|---|---|---|---|---|---|---|
| 3% $H_2O_2$ Wipe | 15 sec | 2% | 30 sec | 7% | 1 min | 24% |
| 3% $H_2O_2$ Wipe with Cold Corona Plasma | 15 sec | 27% | 30 sec | 56% | 1 min | 100% |

It can be observed that the exposure time increased the % kill for the hydrogen peroxide wipe. However, at 15 sec the % kill was quite low for the wipe. On combining the wipe with plasma, the potency of the wipe was increased as observed by the increase in the % kill. These experiments were conducted as a proof of concept to show that cold corona plasma can increase the potency of hydrogen peroxide.

FIG. 30 illustrates an embodiment having a nebulizer transducer, generally 268, such as an ultrasonic transducer 269, arranged to interact with an installed wipe 100. In the embodiment illustrated in FIG. 30, a plurality of optional brush elements 270 constitutes compliant ultrasonic extension elements that provide a degree of conformation of an installed wipe 100 to an irregular surface. A variety of nebulizing transducers are workable, including piezo, mechanical, and atomizing. A less preferred nebulizer includes a heat-activated nebulizer.

In certain embodiments, such as when a wipe 100 carries a fluidized chemical treatment agent, for example Hydrogen Peroxide, and a transducer 268 is embodied as a nebulizer to convert the Hydrogen Peroxide into micron- or nano-sized particles, the system 250 illustrated in FIG. 30 acts as an applicator of energized treatment agent to apply energized treatment agent as a localized fog onto a treatment site or surface, and the energized treatment agent is wiped by an installed disposable wipe 100. Sometimes, an independently operated plain wipe 100 (i.e., dry) may also be used, in combination with an embodiment such as illustrated in FIG. 30 and particularly described here, to remove residual treatment agent from the surface.

Figure 31:
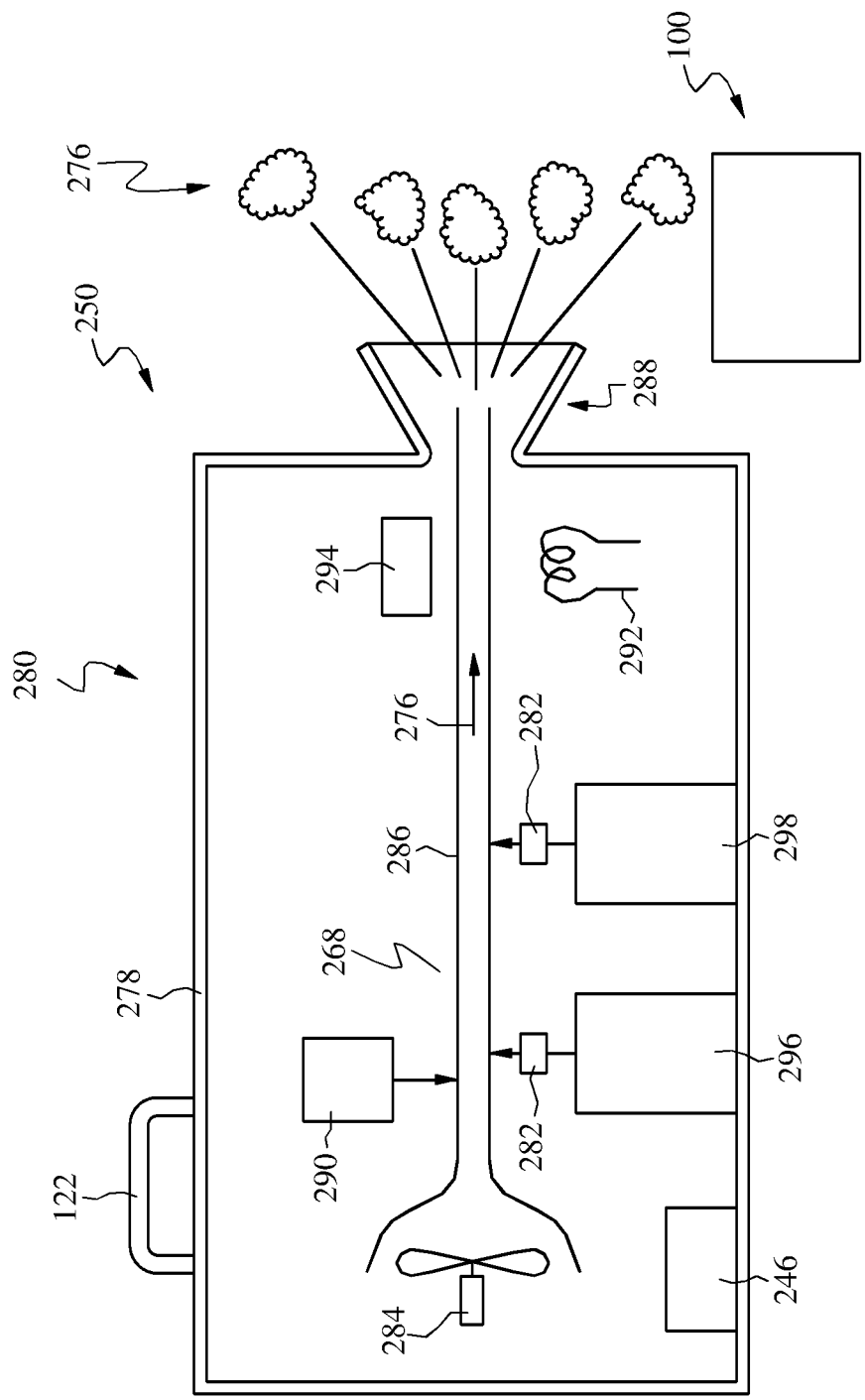
FIG. 31 is a pictorial view in elevation of a wipe in combination with another embodiment of an applicator having an energizing transducer adapted to modify particulate size of a treatment agent, and illustrating several optional features.

FIG. 31 illustrates another embodiment 250 of an applicator of energized treatment agent, generally 276. The embodiment 250 in FIG. 31 includes a housing 278 that may be associated with any of a plurality of energizing elements. As illustrated, housing 278 has a handle 122, which is structured to receive a human hand for manipulation of the housing 278 to deodorize, disinfect, and/or sterilize a treatment site. A preferred housing 278 is adapted for portable use as a stand-alone applicator, generally 280, and includes a portable power/control system 246.

A stand-alone applicator, such as applicator 280, may be used to apply energized treatment agent 276 to a surface independent of a wipe 100. In that case, a wipe 100 may be used to spread the treatment agent, apply a scrubbing action, and/or to remove the treatment agent from the treated surface. Further, the wipe 100 may even be a plain wipe, lacking in treatment agent. An exemplary operable wipe 100 for use with a stand-alone applicator 280 includes a paper towel, cotton cloth, and the like.

Typically, a housing 278 of a stand-alone applicator 280 holds at least one transducer, generally 268, effective to modify the size of treatment agent particles to create a discharge of fog particles having micro- or nano-sizes. An exemplary energizing transducer 268 is a nebulizer 282. Operable particle size-modifying transducers 268 have been described above, in connection with other embodiments, and non-exclusively include ultrasonic and piezo-activated transducers. Thermally actuated nebulizers are less preferred.

In FIG. 31, a fan 284 is provided to urge movement of energized treatment agent 276 along a guide 286 for discharge through an exhaust port, generally 288. Typically, the discharged treatment agent 276 can be characterized as being in a fog-state.

As illustrated in FIG. 31, a housing 278 may hold a plurality of transducers 268, which can include a plurality of nebulizers 282, among other different or similar transducers and treatment-modifying elements. As illustrated, an ion generator 290 may be placed in operable association for inclusion of ions in the discharged fog. Sometimes, a germicidal lamp 292 may be disposed to act on treatment agent. An exemplary germicidal lamp may be a UV lamp, and is typically selected to have an output wavelength in the range between about 250 to about 350 nm. It is also within contemplation that a cold plasma generator 294 may be included in certain embodiments 280. Other transducers within contemplation include a fluid atomizer, and an Ozone generator.

Applicators of energized treatment agent 250 may be embodied to include more than one treatment agent for application of a compound mixture of treatment agents to a treatment site. For example, the stand-alone applicator 280 in FIG. 31 includes a first container 296 in which to hold a quantity of a first fluidized treatment agent, and a second container 298 in which to hold a quantity of a second fluidized treatment agent. A preferred first treatment agent is Hydrogen Peroxide. However, an operable first treatment agent may be selected from the group including (Hydrogen peroxide, Sodium Peroxide, Peracetic acid, Ammonium quaternary compounds, Alcohol in general, Benzyl alcohol, Sodium Hypochlorite, Acetic acid, Silver Nitrate, and Silver citrate). An operable second treatment agent may be selected from that same group.

One method for treating (e.g., deodorizing, disinfecting, or sterilizing) a surface includes the steps of: providing a holder structured in harmony with a disposable wipe to create micron- or nano-sized particles of a first treatment agent carried by the wipe and selected from the group consisting of (Hydrogen peroxide, Sodium Peroxide, Peracetic acid, Ammonium quaternary compounds, Alcohol (e.g., Benzyl or other effective alcohol), Sodium Hypochlorite, Acetic acid, Silver Nitrate, and Silver citrate), and/or to create hydroxyl or other chemical radicals from a portion of the first chemical treatment agent; placing a disposable wipe in operable registration with the holder; and treating a surface of an object by activating the holder to energize a portion of the first treatment agent and wiping the object with the disposable wipe.

Another operable method may include providing an applicator structured to create a fog of micron- or nano-sized particles of a first chemical treatment agent selected from the group (Hydrogen peroxide, Sodium Peroxide, Peracetic acid, Ammonium quaternary compounds, Alcohol, Sodium Hypochlorite, Acetic acid, Silver Nitrate, and Silver citrate), and/or to create hydroxyl or other chemical radicals from a portion of the first chemical treatment agent; treating a surface of an object by applying the fog and/or chemical radicals onto the object with the applicator; and wiping the surface with a disposable wipe.

The invention may be practiced in a method that may further include a pre-treatment step including application of a surface treatment to the surface to be treated that enhances the hydrophilic status of the surface. An exemplary surface treatment may be selected from chemical surfactant, and plasma. In some cases, the applicator used in a method according to certain principles of the invention may be, or include, the disposable wipe.

While the invention has been described in particular with reference to certain illustrated embodiments, such is not intended to limit the scope of the invention. The present invention may be embodied in other specific forms without departing from its spirit or essential characteristics. For example, one or more element may be extracted from any described embodiment for use on its own, and/or combined with one or more element from any other embodiment to form an alternative embodiment according to certain principles of the invention. The described embodiments are to be considered as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method, comprising:
providing a holder structured in harmony with a disposable wipe to create hydroxyl or other chemical radicals from a portion of a first chemical treatment agent, the holder comprising a power source and a control system operably coupled to an electrically activated first transducer, the holder being configured to receive individual ones of a plurality of disposable wipes in successive installed operable registration with the holder;
placing a disposable wipe in operable registration with the holder, the disposable wipe carrying the first chemical treatment agent; and
treating a surface of an object by activating the holder to energize a portion of the first treatment agent and thereby modify the first treatment agent such that modified treatment agent is energized and is improved in efficacy to kill microbes compared to unmodified treatment agent, and wiping the object with the disposable wipe.

2. A method, comprising:
providing an applicator of energized treatment agent, the applicator comprising a power source and a control system operably coupled to an energizing transducer to create a fog of micron- or nano-sized particles of liquid comprising a first chemical treatment agent selected from the group consisting of Hydrogen peroxide, Sodium Peroxide, Peracetic acid, Ammonium quaternary compounds, Alcohol, Sodium Hypochlorite, Acetic acid, Silver Nitrate, and Silver citrate, the energized treatment agent being a modified form of the first chemical treatment agent and having an enhanced power to kill microbes compared to the unmodified first chemical treatment agent;
treating a surface of an object by applying the fog onto the object with the applicator; and
wiping the surface with a disposable wipe, wherein:
the applicator and wipe, in combination, are configured to create hydroxyl radicals to further enhance efficacy of cleaning.

3. The method according to claim 2, further comprising:
a pre-treatment step comprising application of a surface treatment to the surface to be treated that enhances the hydrophilic status of the surface.

4. The method according to claim 3, wherein:
the surface treatment is selected from the group consisting of: chemical surfactant, and plasma.

5. The method according to claim 2, wherein:
the applicator further comprises the disposable wipe.

6. The method according to claim 1, wherein:
the first transducer comprises a cold plasma generator arranged to impart plasma to a wipe at a wipe-support surface; the method further comprising:
operating the control system to generate the chemical radicals on demand.

7. The method according to claim 1, wherein:
the first transducer is a fluid particle size-modifying transducer configured to create micron- or nano-sized particles of the first treatment agent, the first treatment agent being selected from the group consisting of Hydrogen peroxide, Sodium Peroxide, Peracetic acid, Ammonium quaternary compounds, Alcohol, Sodium Hypochlorite, Acetic acid, Silver Nitrate, and Silver citrate; the method further comprising:

operating the control system to generate the micron- or nano-sized particles on demand.

8. The method according to claim 6, wherein:
the holder comprises a housing in which to receive a human hand; and
the method further comprises substantially enclosing the housing inside an open-ended envelope defined by a wipe prior to the step of generating the chemical radicals.

9. The method according to claim 6, wherein:
the holder comprises a second transducer operably associate with the control system, the second transducer being configured to create micron- or nano-sized particles of the first treatment agent; the method further comprising:
operating the control system to generate the micron- or nano-sized particles on demand.

10. The method according to claim 6, wherein:
the holder comprises a second transducer operably associate with the control system, the second transducer a UV light; the method further comprising:
operating the control system energize the UV light on demand.

11. The method according to claim 6, wherein:
the holder comprises a second transducer operably associate with the control system, the second transducer being configured to create an ion treatment agent; the method further comprising:
operating the control system to generate ions on demand.

12. The method according to claim 6, wherein:
the holder is compliant and permits application to, and contact of a wipe with, an irregular, non-flat, or curved surface.

13. The method according to claim 1, wherein:
the holder comprises biased first and second attachment mechanisms, the first and second attachment mechanisms being disposed spaced apart to hold a disposable wipe there-between such that an installed wipe spans across an activation surface; and
the method further comprises:
installing a wipe in engagement with the first and second attachment mechanisms such that a wipe surface is placed into contact with said first transducer; and
operating the control system to cause the first transducer to energize the portion of first treatment agent.

* * * * *